US007507337B2

(12) United States Patent
Petro et al.

(10) Patent No.: US 7,507,337 B2
(45) Date of Patent: Mar. 24, 2009

(54) SYSTEM AND METHOD FOR RAPID CHROMATOGRAPHY WITH FLUID TEMPERATURE AND MOBILE PHASE COMPOSITION CONTROL

(75) Inventors: Miroslav Petro, San Jose, CA (US); Gary M. Diamond, San Jose, CA (US); Thomas Harding McWaid, Fremont, CA (US); Keith Anthony Hall, San Jose, CA (US); Li Song, Santa Clara, CA (US); Trevor G. Frank, Fremont, CA (US)

(73) Assignee: Symyx Technologies, Inc., Sunnyvale, CA (US)

( * ) Notice: Subject to any disclaimer, the term of this patent is extended or adjusted under 35 U.S.C. 154(b) by 676 days.

(21) Appl. No.: 11/219,073

(22) Filed: Sep. 2, 2005

(65) Prior Publication Data

US 2006/0054543 A1 Mar. 16, 2006

Related U.S. Application Data

(60) Provisional application No. 60/607,032, filed on Sep. 3, 2004.

(51) Int. Cl.
*B01D 15/08* (2006.01)
(52) U.S. Cl. .................... 210/198.2; 210/656; 210/101; 210/143; 210/181
(58) Field of Classification Search ................ 210/635, 210/656, 659, 101, 143, 181, 198.2
See application file for complete search history.

(56) References Cited

U.S. PATENT DOCUMENTS

| 3,773,470 | A | 11/1973 | Rouzier ........................ 23/252 |
| 4,036,063 | A | 7/1977 | Roof et al. ..................... 73/422 |
| 4,239,623 | A | 12/1980 | Schrenker ................... 210/96.1 |
| 4,258,564 | A | 3/1981 | Hulme et al. ................. 73/61.1 |
| 4,268,241 | A | 5/1981 | Rees ........................... 425/549 |

(Continued)

FOREIGN PATENT DOCUMENTS

CH          648486          3/1985

(Continued)

OTHER PUBLICATIONS

*Author*: Petro et al. *Publish Date*: *Publish Year*:1997 vol. 69 pp. 3131-3139 *Journal*: Anal. Chem. *Title*: Monodisperse Hydrolyzed Poly(glycidyl methacrylate-co-ethylene dimethacrylate) Beads As A Staionary Phase For Normal-Phase HPLC.

(Continued)

*Primary Examiner*—Ernest G Therkorn
(74) *Attorney, Agent, or Firm*—Scott D. Rothenberger

(57) ABSTRACT

The invention relates to liquid chromatography techniques for rapidly characterizing samples, such as polymer solutions, emulsions and dispersions, and to devices for implementing such techniques. The system includes a design that provides the ability to perform chromatographic separations by using mobile phase composition gradients and temperature gradients during separations. The invention accomplishes this by providing mixing zones for a plurality of fluids as well as heated and chilled feeds feeding the fluids to the mixing zones. Additionally, the system provides the ability to analyze separated components with a detector and/or collect separated fractions into vessels of a fraction collector for further separation and/or analysis.

32 Claims, 15 Drawing Sheets

U.S. PATENT DOCUMENTS

| | | | | |
|---|---|---|---|---|
| 4,271,703 A | | 6/1981 | Roof | 73/863.11 |
| 4,294,799 A | | 10/1981 | Stephens et al. | 422/62 |
| 4,315,754 A | | 2/1982 | Ruzicka et al. | 23/230 R |
| 4,399,225 A | | 8/1983 | Hansen et al. | 436/34 |
| 4,406,158 A | | 9/1983 | Allington | 73/61.1 C |
| 4,479,380 A | | 10/1984 | Novotny et al. | 73/61.1 C |
| 4,532,043 A | | 7/1985 | Prudhomme et al. | 210/635 |
| 4,534,941 A | | 8/1985 | Stephens et al. | 422/70 |
| 4,674,323 A | | 6/1987 | Rulf et al. | 73/61.1 |
| 4,695,430 A | | 9/1987 | Coville | 422/65 |
| 4,728,344 A | | 3/1988 | Stacy | 55/67 |
| 4,775,476 A | | 10/1988 | Melcher et al. | 210/635 |
| 4,798,081 A | | 1/1989 | Hazlitt et al. | 73/53 |
| 4,816,226 A | | 3/1989 | Jordan et al. | 422/81 |
| 4,837,161 A | * | 6/1989 | Stevens et al. | 436/52 |
| 4,882,781 A | | 11/1989 | Allington | 364/510 |
| 4,930,898 A | | 6/1990 | Miller-Ihli | 366/109 |
| 4,942,018 A | | 7/1990 | Munk | 422/70 |
| 4,962,662 A | | 10/1990 | Berger | 73/23.42 |
| 4,966,695 A | | 10/1990 | Joshua | 210/198.2 |
| 4,969,993 A | | 11/1990 | Nash, Jr. et al. | 210/198.2 |
| 4,980,130 A | | 12/1990 | Metzger et al. | 422/70 |
| 4,982,597 A | | 1/1991 | Berger | 73/23.1 |
| 4,988,447 A | | 1/1991 | Hellinger | 210/659 |
| 4,992,168 A | | 2/1991 | Takayama et al. | 210/198.2 |
| 5,004,546 A | | 4/1991 | Takahashi et al. | 210/635 |
| 5,008,204 A | | 4/1991 | Stehling | 436/85 |
| 5,037,396 A | | 8/1991 | Streeter | 604/152 |
| 5,039,614 A | | 8/1991 | Dekmezian et al. | 436/43 |
| 5,185,429 A | | 2/1993 | Cinquina et al. | 528/503 |
| 5,238,653 A | | 8/1993 | Bourne | 422/70 |
| 5,277,871 A | * | 1/1994 | Fujii et al. | 422/70 |
| 5,287,758 A | | 2/1994 | Geiss et al. | 73/864.01 |
| 5,290,520 A | | 3/1994 | Maystre et al. | 422/82.05 |
| 5,305,073 A | | 4/1994 | Ford, Jr. | 356/338 |
| 5,334,310 A | | 8/1994 | Frechet et al. | 210/198.2 |
| 5,372,721 A | | 12/1994 | Langhorst et al. | 210/635 |
| 5,441,700 A | | 8/1995 | Markelov | 422/83 |
| 5,474,744 A | | 12/1995 | Lerch | 422/100 |
| 5,508,204 A | | 4/1996 | Norman | 436/161 |
| 5,597,733 A | | 1/1997 | Bell et al. | 436/54 |
| 5,665,311 A | | 9/1997 | Gorog | 422/73 |
| 5,738,783 A | | 4/1998 | Shirota et al. | 210/198.2 |
| 5,741,709 A | | 4/1998 | Hsu | 436/52 |
| 5,746,982 A | | 5/1998 | Saneii et al. | 422/134 |
| 5,747,102 A | | 5/1998 | Smith | 427/96 |
| 5,773,305 A | | 6/1998 | Zabetakis et al. | 436/179 |
| 5,776,359 A | | 7/1998 | Schultz et al. | 252/62.51 |
| 5,777,213 A | | 7/1998 | Tsukazaki et al. | 73/61.25 |
| 5,814,742 A | | 9/1998 | Vissers et al. | 73/863.73 |
| 5,868,710 A | | 2/1999 | Battiato | 604/123 |
| 5,871,786 A | | 2/1999 | Hume | 425/549 |
| 5,882,343 A | | 3/1999 | Wilson | 604/246 |
| 5,897,837 A | | 4/1999 | Mizuno | 422/100 |
| 5,959,297 A | | 9/1999 | Weinberg et al. | 250/288 |
| 5,983,710 A | | 11/1999 | Uhen et al. | 73/61.52 |
| 6,063,283 A | | 5/2000 | Shirota et al. | 210/656 |
| 6,064,945 A | | 5/2000 | Gorenstein et al. | 702/23 |
| 6,074,879 A | | 6/2000 | Zelmanovic et al. | 436/10 |
| 6,175,409 B1 | | 1/2001 | Nielsen et al. | 356/337 |
| 6,221,045 B1 | | 4/2001 | Duchon | 604/151 |
| 6,260,407 B1 | | 7/2001 | Petro et al. | 73/61.52 |
| 6,265,226 B1 | | 7/2001 | Petro | 436/180 |
| 6,294,388 B1 | | 9/2001 | Petro | 436/8 |
| 6,296,771 B1 | | 10/2001 | Miroslav | 210/656 |
| 6,306,658 B1 | | 10/2001 | Turner et al. | 436/37 |
| 6,345,528 B2 | | 2/2002 | Petro et al. | 73/61.52 |
| 6,406,632 B1 | | 6/2002 | Safir et al. | 210/656 |
| 6,492,184 B1 | | 12/2002 | Petro | 436/180 |
| 6,541,304 B1 | | 4/2003 | Bouras | 438/108 |
| 6,562,232 B2 | | 5/2003 | Myogadani | 210/94 |
| 6,720,186 B1 | | 4/2004 | Turner | 436/37 |
| 6,730,228 B2 | | 5/2004 | Petro et al. | 210/656 |
| 6,742,544 B2 | | 6/2004 | Bergh | 137/885 |
| 6,755,074 B2 | | 6/2004 | Davison et al. | 73/61.55 |
| 6,756,195 B2 | | 6/2004 | Weinberg | 435/4 |
| 6,855,258 B2 | | 2/2005 | Petro et al. | 210/656 |
| 6,866,786 B2 | | 3/2005 | Petro et al. | 210/656 |
| 2003/0080062 A1 | | 5/2003 | Petro et al. | 210/656 |
| 2005/0236314 A1 | * | 10/2005 | Neyer et al. | 210/198.2 |

FOREIGN PATENT DOCUMENTS

| | | |
|---|---|---|
| DE | 39 09 599 | 9/1990 |
| DE | 4102336 | 8/1992 |
| EP | 0 380 864 | 8/1990 |
| EP | 0 665 433 | 8/1995 |
| JP | 63-135857 | 6/1988 |
| JP | 1-98963 | 4/1989 |
| JP | 89-98963 | 4/1989 |
| JP | 410010104 | 1/1998 |
| WO | WO 96/11878 | 4/1996 |
| WO | WO 98/10279 | 3/1998 |

OTHER PUBLICATIONS

*Author*: Petro et al. *Publish Date: Publish Year*:1996 vol. 68 pp. 315-321 *Journal*: Anal. Chem. *Title*: Molded Monolithic Rod Of macroporous Poly(styrene-co-divinylbenzene) As A Separation Medium For HPLC Of Synthetic Polymers: On-Column Precipitation-Redissolution Chromatography As An Alternative To.

*Author*: Petro et al. *Publish Date: Publish Year*:1996 vol. 49 pp. 355-363 *Journal*: Biotech *Title*: Immmobilization Of Trypsin Onto Molded Macroporous Poly(Glycidyl Methacrylate-co-Ethylene Dimethacrylate) Rods And Use Of Conjugates As Bioreactors And For Affinity Chromatography.

*Author*: Petro et al. *Publish Date: Publish Year*:1996 vol. 752 pp. 59-66 *Journal*: Journal Of Chromatography *Title*: Molded Continuous Poly(Styrene-co-divinylbenzene) Rod As A Separation Medium For The Very Fast Separation Of Polymers Comparison Of The Chromatographic Properties Of The Monolithic Rod With Columns.

*Author*: Poche et al. *Publish Date: Publish Year*:1997 vol. 64(8) pp. 1613-1623 *Journal*: J. Applied Polymer Science *Title*: Use Of laboratory Robotics For Gel Permeation Chromatography Sample Preparation: Automation Of High-Temperature Polymer Dissolution.

*Author*: Odian *Publish Date: Publish Year*:1991 *Volume: Pages: Journal*: Book *Title*: Principles of Polymerization.

*Author*: Xu et al. *Publish Date: Publish Year*:2000 vol. 36 pp. 867-878 *Journal*: Eur. Polym J. *Title*: Application of Temperature Rising Elution Fractionation in Polyolefins.

*Author*: Daoust et al. *Publish Date: Publish Year*:2001 vol. 42 pp. 1953-1967 *Journal*: Polymer *Title*: Characterization of the Molecular Structure of Two Highly Isotactic Polypropylenes.

*Author*: Boborodea et al. *Publish Date: Publish Year*:2004 vol. 22(1) pp. 4 pages *Journal*: LCGC North America *Title*: An Improved Analytical Temperature-Rising Elution Fractionation System for Automated Analysis of Polyethylenes.

*Author*: Trumbore et al. *Publish Date: Publish Year*:1985 vol. 322 pp. 443-454 *Journal*: Journal Of Chromatography *Title*: Further Experiments On A New Fast Method For Determining Molecular Weights Of Diffusing Species In A Liquid Phase.

*Author*: Barth et al. *Publish Date: Publish Year*:1998 vol. 70 pp. 251-278 *Journal*: Anal. Chem. *Title*: Size Exclusion Chromatography And Related Separation Techniques.

*Author*: Fotheringham et al. *Publish Date: Publish Year*:1998 *Volume*: pp. 25-32 *Journal*: American Laboratory *Title*: An Integrated GPC-SEC System for Room-Temperature and High-Temperature Polymer Characterization.

*Author*: Stulik, Karel *Publish Date: Publish Year*:1993 vol. 273 pp. 435-441 *Journal*: Analytica Chimica Acta. *Title*: Electrochemical Detection For Flow Analysis And Liquid Chromatography: Present Status And Some Roads To The Future.

*Author*: Taylor et al. *Publish Date: Publish Year*:1995 vol. 29009 pp. 691-700 *Journal*: SPE Symposium *Title*: Development Of A Flow Injection Analysis Method For The Determination Of Acrylamide Copolymers In Oilfield Brines.

*Author*: Taylor et al. *Publish Date: Publish Year*:1998 vol. 21 pp. 129-139 *Journal*: J. Petroleum Science And Engin. *Title*: Development Of A Flow Injection Analysis Method For The Determination Of Acrylamide Copolymers In Brines.

*Author*: Tessema et al. *Publish Date: Publish Year*:1997 vol. 349 pp. 179-188 *Journal*: Analytica Chimica Acta. *Title*: Simultaneous Amerometric Determination Of SOme Mono-, Di-, And Oligosacchrides In Flow Injection And Liquid Chromatography Using Two Working Enzyme Electrodes with Different Selectivity.

*Author*: Olson et al. *Publish Date*:Sep. 1, 1997 *Publish Year*: vol. 69 (17) pp. 3496-3505 *Journal*: Anal. Chem. *Title*: Dynamic Surface Tension And Adhesion Detection For The Rapid Analysis Of Surfactants In Flowing Aqueous Liquids.

*Author*: Ouano *Publish date: Publish Year*:1973 vol. 43 pp. 299-310 *Journal*: Journal Of Polymer Science *Title*: Gel Permeation Chromatography VII. Molecular Weight Detection Of GPC Effluents.

*Author*: Petro et al. *Publish Date: Publish Year*:1997 *Volume*: pp. 1173-1180 *Journal*: Chromatography of Functional Polymers *Title*: Chromatography Of Functional Polymers: A New Approach To The Characterization Of Reactive Polymers Obtained By Chemical Modification.

*Author*: Hancock et al. *Publish Date: Publish Year*:1988 vol. 60 pp. 2812-2818 *Journal*: Anal. Chem. *Title*: Rapid Characterization Of Linear And Star-Branched Polymers By Concentration Gradient Detection.

*Author*: Mendichi et al. *Publish Date: Publish Year*:1998 vol. 65 pp. 1651-1659 *Journal*: J. Applied Polymer Science *Title*: Evaluation Of A SIngle-Capillary Viscometer Detector On Line To A SEC System Used With A New Pulse-Free Pump.

*Author*: Lesec et al. *Publish Date: Publish Year*:1993 vol. Ch.14 pp. 220-230 *Journal*: Chromatography Of Polymers *Title*: Single-Capillary Viscometer Used FOr Accurate Determination Of Molecular Weights And Mark-Houwink Constants.

*Author*: Monnig et al. *Publish Date*:Apr. 15, 1991 *Publish Year*: vol. 63(8) pp. 807-810 *Journal*: Anal. Chem. *Title*: Sample Gating In Open Tubular And Packed Capillaries For High-Speed Liquid Chromatography.

*Author*: Trathnigg et al. *Publish Date: Publish Year*:1999 *Volume*: pp. 190-199 *Journal*: Chromatography Of Polymers *Title*: Two-Dimensional Liquid Chromatography Of Functional Polyethers.

*Author*: Jiang et al. *Publish Date: Publish Year*:2000 *Volume*: pp. 98-108 *Journal*: American Laboratory *Title*: Characterization of Water-Soluble Polymers by Flow FFF-MALS.

*Author*: Atiqullah et al. *Publish Date: Publish Year*:1994 vol. 35 pp. 765-770 *Journal*: Polymer *Title*: Optimized Calibration Curve for Size Exclusion Chromatography Applied to Poly (Vinyl Chloride).

*Author*: Cools et al. *Publish Date: Publish Year*:1996 vol. 736 pp. 125-130 *Journal*: Journal Of Chromatography *Title*: Determination of the Chemical Composition Distribution of Copolymers of Styrene and Butadiene by Gradient Polymer Elution Chromatography.

*Author*: Staal et al. *Publish Date: Publish Year*:1994 vol. 17 pp. 3191-3199 *Journal*: Journal Of Liquid Chromatography *Title*: Monitoring of Originated Polymer in Pure Monomer with Gradient Polymer Elution Chromatography (GPEC).

*Author*: Balke et al. *Publish Date: Publish Year*:1990 vol. 13 pp. 2929-2955 *Journal*: Journal Of Liquid Chromatography *Title*: Quantitative Size Exclusion Chromatography: Assessing New Developments.

*Author*: Hester et al. *Publish Date: Publish Year*:1980 vol. 18 pp. 1727-1738 *Journal*: J. Polymer Sci. *Title*: A New Universal GPC Calibration Method.

*Author*: Lecacheux et al. *Publish Date: Publish Year*:1982 vol. 5 pp. 217-228 *Journal*: Journal Of Liquid Chromatography *Title*: Gel Permeation Chromatography: Problems Caused by Polydispersity in the Application of the Benoit's Universal Parameter.

*Author*: Pigeon et al. *Publish Date: Publish Year*:1995 vol. 57 pp. 287-301 *Journal*: J. Applied Polymer Science *Title*: Correction for Interdetector Volume in Size Exclusion Chromatography (SEC).

*Author*: Puskas et al. *Publish Date: Publish Year*:1993 vol. 66 pp. 742-748 *Journal*: Rubber Chem. Technol. *Title*: GPC Calibration for the Molecular Weight Measurement of Butyl Rubbers.

*Author*: Rosset et al. *Publish Date: Publish Year*:1994 vol. 22 pp. 293-304 *Journal*: Analysis *Title*: Nouvelles Methodes d\'Etalonnage en Chromatographie d\'Exclusion Sterique.

*Author*: Rudin et al. *Publish Date: Publish Year*:1972 vol. 10 pp. 217-235 *Journal*: Journal of Polymer Science *Title*: Universal Calibration in GPC.

*Author*: Philipsen et al. *Publish Date: Publish Year*:1996 vol. 746 pp. 211-224 *Journal*: Journal of Chromatography *Title*: Characterization of Low-Molar-Mass Polymers by Gradient Polymer Elution Chromatography I. Practical Parameters and Applications of the Analysis of Polyester Resins Under Reversed Phase Conditions.

*Author*: Gilson, Inc. *Publish Date: Publish Year*:1994 *Volume*: pp. 8 pages *Journal*: Brochure *Title*: Gilson 231 XL and 232 XL Sampling Injectors.

*Author*: Bond et al. *Publish Date: Publish Year*:1991 *Volume*: April pp. 114-116 *Journal*: Chemistry In Australia *Title*: Electrochemical Analysis in Flowing Solutions.

*Author*: Boyle et al. *Publish Date: Publish Year*:1991 vol. 42 pp. 1969-1977 *Journal*: J. Applied Polymer Science *Title*: Flow Injection Analysis Estimation of Diffusion Coefficients of Pauci- and Polydisperse Polymers Such as Polystyrene Sulfonates.

*Author*: Creasy et al. *Publish Date: Publish Year*:1995 *Volume*: January pp. 416-422 *Journal*: Journal of Process Analytical Chemistry *Title*: Flow Injection Analyzer Equipped with Infrared Detection for Monitoring Chemical Processes.

*Author*: Davidson et al. *Publish Date: Publish Year*:1971 vol. 35 pp. 235-255 *Journal*: J. Polymer Sci. *Title*: Latex Particle Size Analysis. Part III. Particle Size Distribution by Flow Ultramicroscopy.

*Author*: Haney *Publish Date: Publish Year*:1985 *Volume*: March pp. 41-56 *Journal*: American Laboratory *Title*: A Differential Viscometer.

*Author*: Muragaiah et al. *Publish Date: Publish Year*:1993 vol. 69 pp. 410-411 *Journal*: Polymeric Materials Science and Engineering (ACS) *Title*: Molecular Weight Determination of Polymers By Flow Injection Analysis and Refractive Index Gradient Detection.

*Author*: Murugaiah et al. *Publish Date: Publish Year*:1994 vol. 581 pp. 25-43 *Journal*: ACS Symp. Ser. *Title*: Determination of Polymer Molecular Weight by Flow Injection Analysis and Refractive Index Gradient Detection.

*Author*: Powell *Publish Date: Publish Year*:1998 vol. 123 pp. 797-802 *Journal*: Analyst *Title*: Application of Flow Injection Analysis Adsorption-Elution Protocols for Aluminum Fractionation.

*Author*: Valcarcel et al. *Publish Date: Publish Year*:1987 *Volume*: pp. 1-400 *Journal*: Book *Title*: Flow-Injection Analysis.

\* cited by examiner

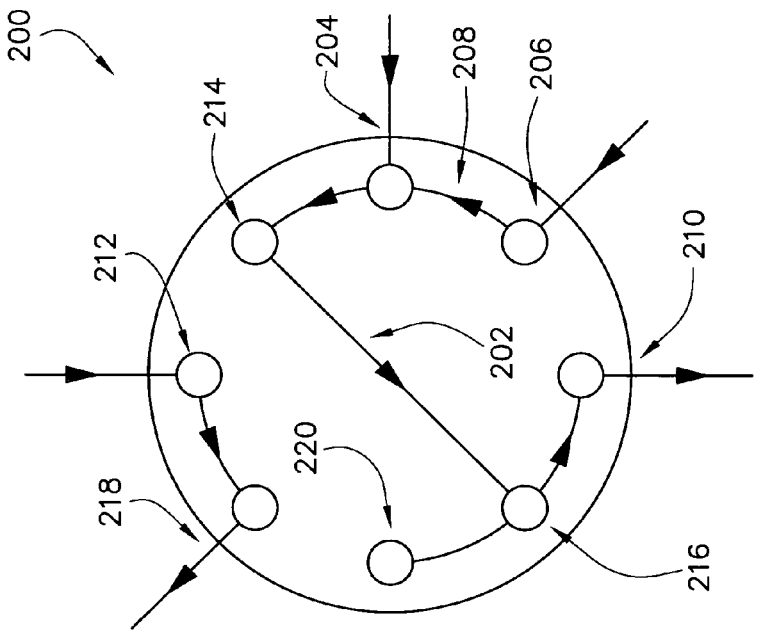
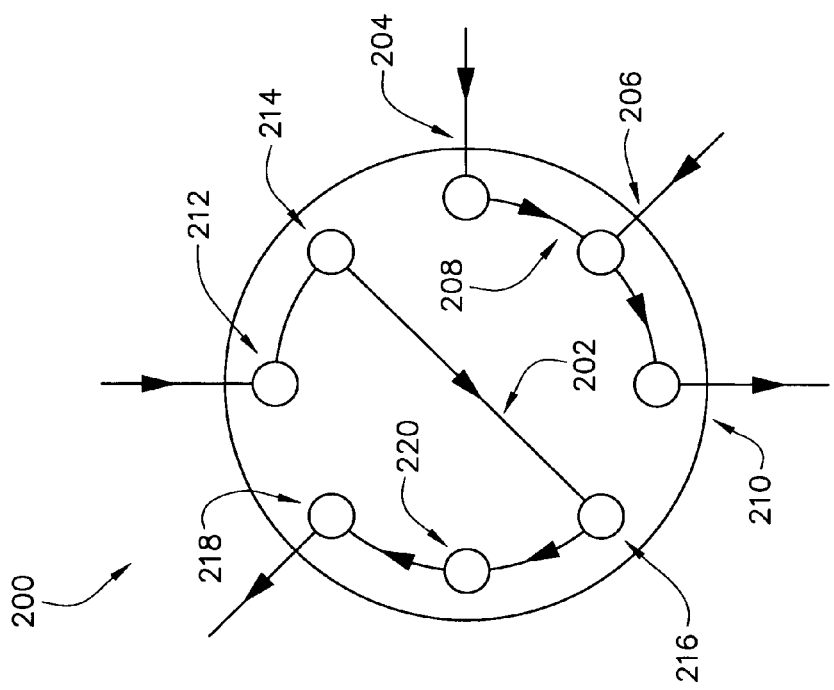

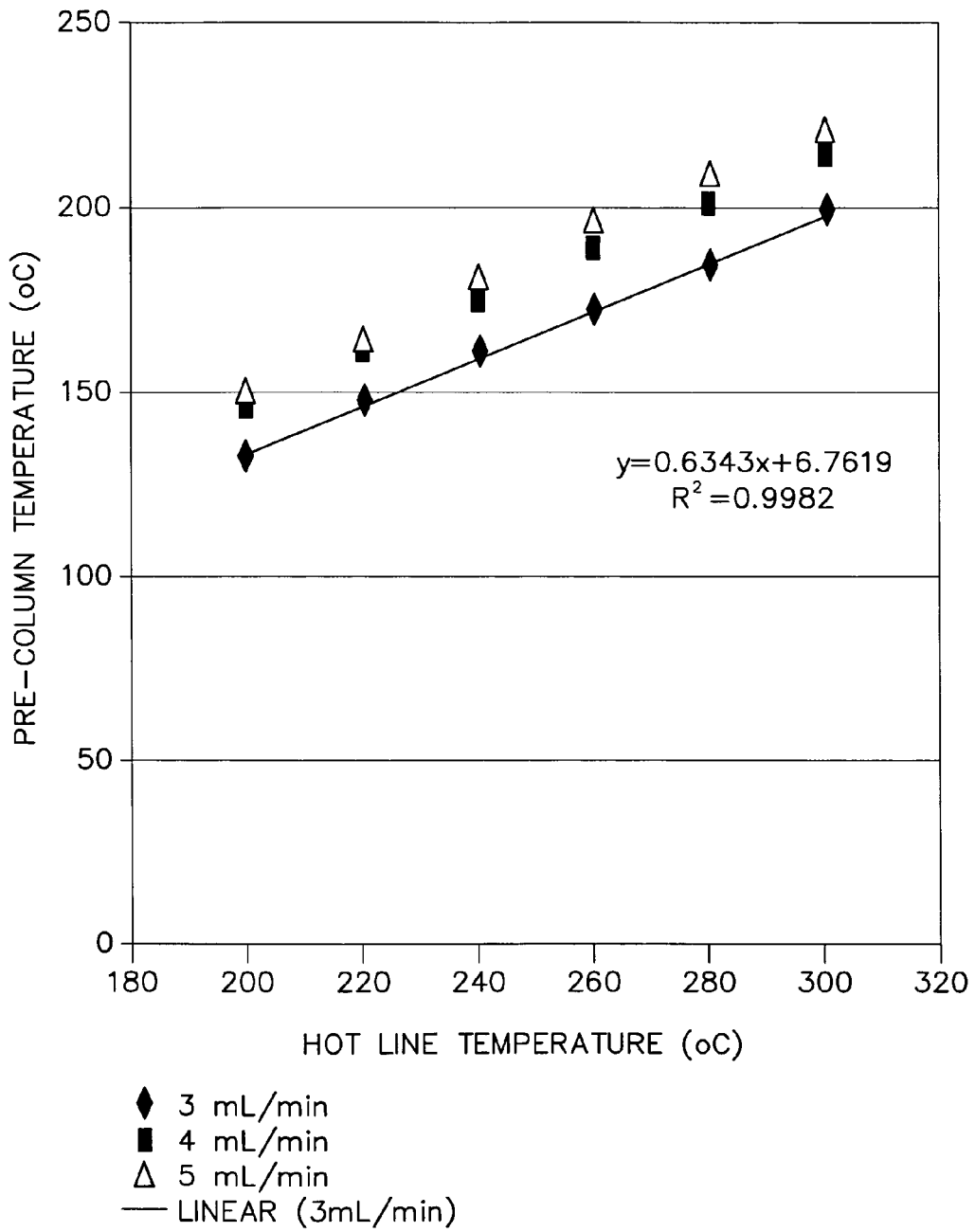

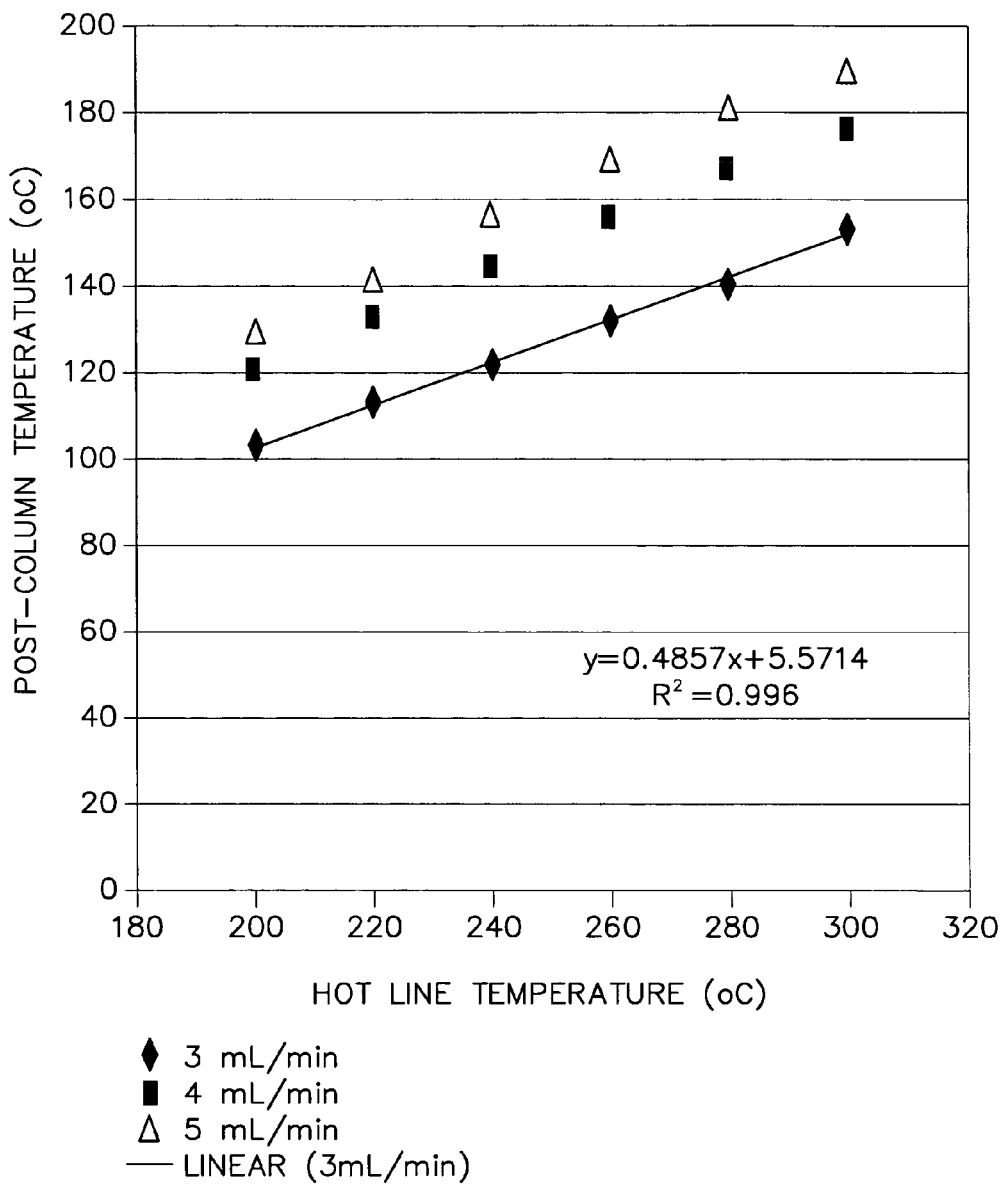

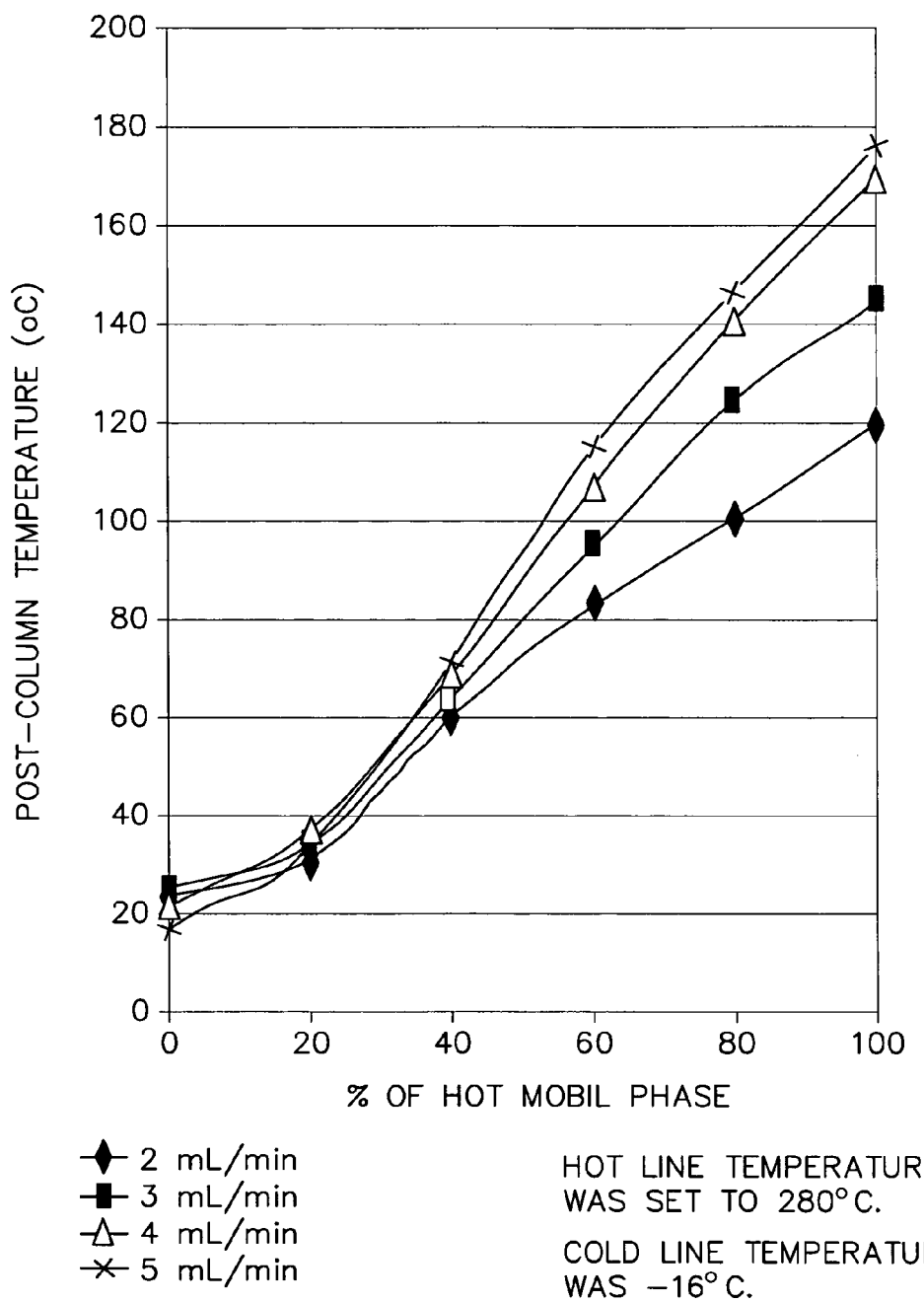

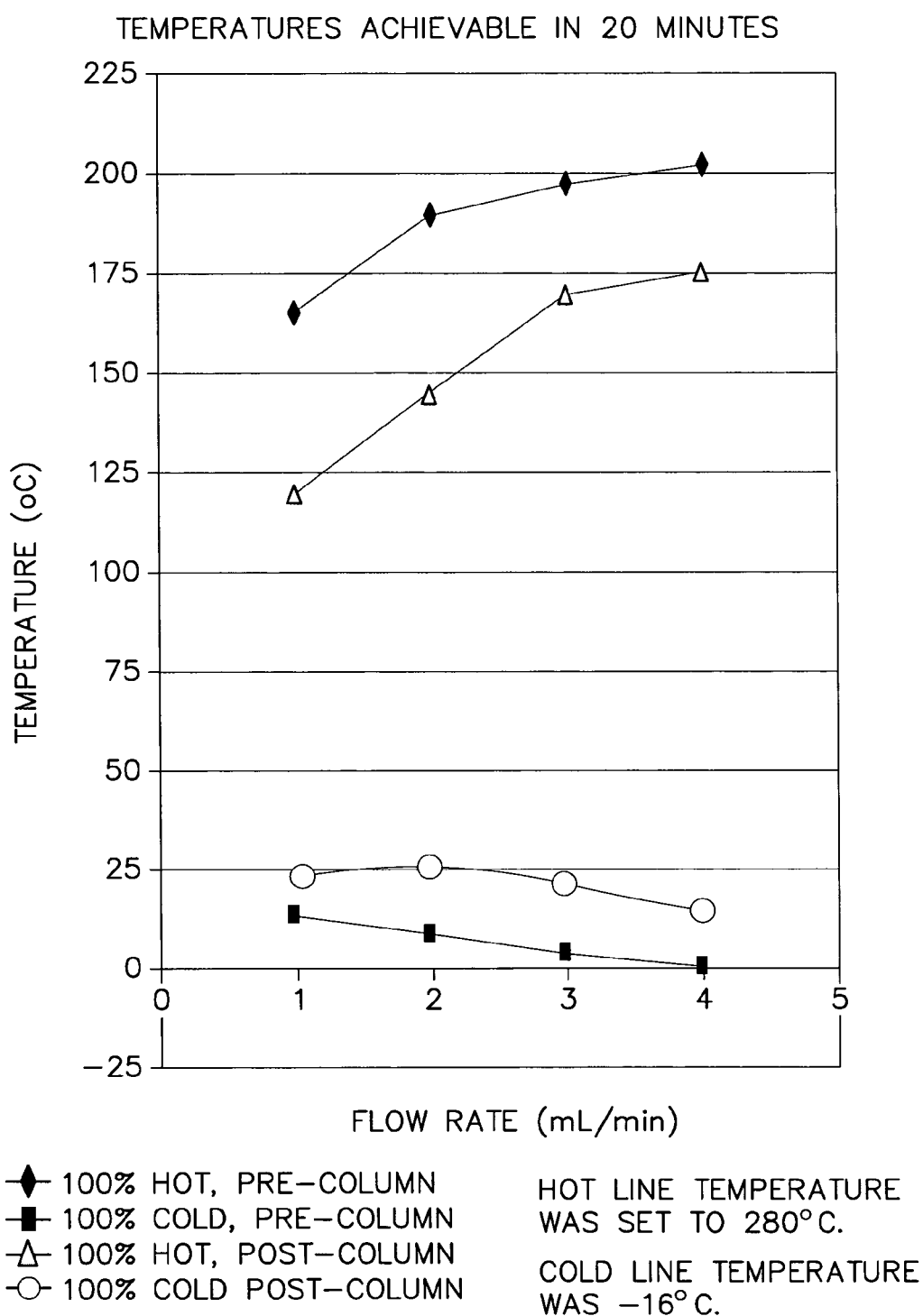

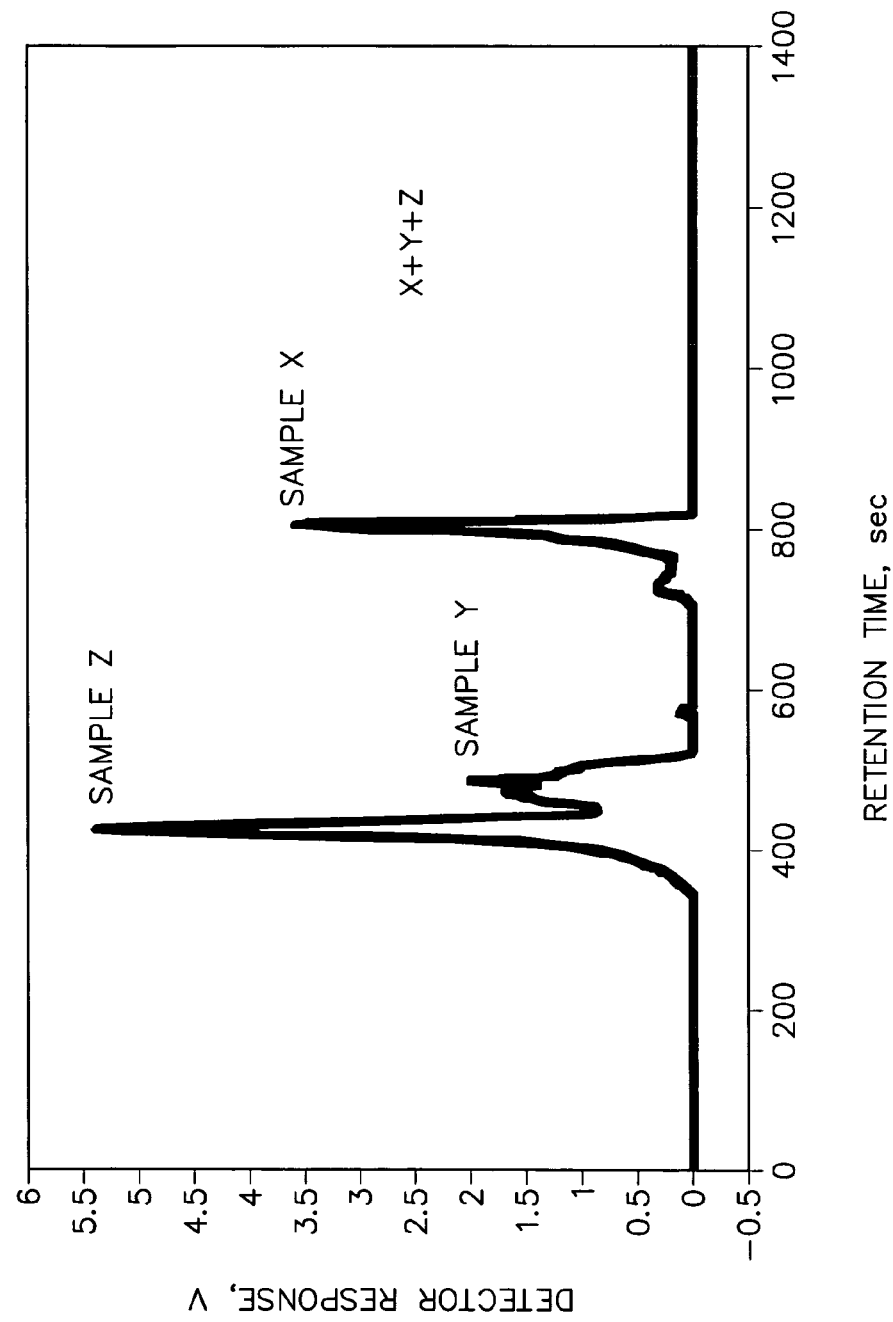

SYSTEM AND METHOD FOR RAPID CHROMATOGRAPHY WITH FLUID TEMPERATURE AND MOBILE PHASE COMPOSITION CONTROL

CLAIM OF PRIORITY

The present invention claims the benefit of the priority of U.S. Provisional Application Ser. No. 60/607,032, filed Sep. 3, 2004, the contents of which is incorporated herein by reference for all purposes.

BACKGROUND OF INVENTION

The present invention generally relates to the field of material characterization. In particular, the invention relates to liquid chromatography techniques for rapidly characterizing and sampling polymer solutions, emulsions and dispersions, and to devices for implementing such techniques. The invention particularly relates to characterization of polymer samples in a comprehensive, directly-coupled, multi-dimensional high-performance liquid chromatography system including HPLC (High Performance Liquid Chromatography) and TREF (Temperature Rising Elution Fractionation)—like conditions in which temperature, and/or solvent gradients in any combination can be used during separation for determining a variety of properties, such as composition and molecular weight or size. The methods and devices disclosed herein are applicable, inter alia, to the rapid and multi-dimensional characterization of libraries of polymers prepared by combinatorial materials science techniques.

Currently, there is substantial research activity directed toward the discovery and optimization of polymeric materials for a wide range of applications. Although the chemistry of many polymers and polymerization reactions has been extensively studied, it is, nonetheless, rarely possible to predict a priori the physical or chemical properties a particular polymeric material will possess or the precise composition and architecture that will result from any particular synthesis scheme. Thus, characterization techniques to determine such properties are an essential part of the discovery process.

Liquid chromatography is well known in the art for characterizing a polymer sample. Liquid chromatographic techniques employ separation of one or more components of a polymer sample from other components thereof by flow through a chromatographic column, followed by detection of the separated components with a flow-through detector. Approaches for liquid chromatography can vary, however, with respect to the basis of separation and with respect to the basis of detection.

Gel permeation chromatography (GPC), a well-known form of size exclusion chromatography (SEC), is a frequently-employed chromatographic technique for polymer size determination. In GPC, the polymer sample is separated into components according to the hydrodynamic volume occupied by each component in solution. More specifically, a polymer sample is injected into a mobile phase of a liquid chromatography system and is passed through one or more chromatographic columns packed with porous beads. Molecules with relatively small hydrodynamic volumes diffuse into the pores of the beads and remain therein for longer periods, and therefore exit the column after molecules with relatively larger hydrodynamic volume. Hence, GPC can characterize one or more separated components of the polymer sample with respect to its effective hydrodynamic radius ($R_h$).

Another chromatographic separation approach is illustrated by U.S. Pat. No. 5,334,310 to Fréchet et al. and involves the use of a porous monolithic stationary-phase as a separation medium within the chromatographic column, combined with a mobile phase composition gradient. (See also, Petro et al, *Molded Monolithic Rod of Macroporous Poly(styrene-co-divinylbenzene) as a Separation Medium for HPLC Synthetic Polymers: "On-Column" Precipitation-Redissolution Chromatography as an Alternative to Size Exclusion Chromatography of Styrene Oligomers and Polymers*, Anal. Chem., 68, 315-321 (1996); and Petro et al, *Immobilization of Trypsin onto "Molded" Macroporous Poly(Glycidyl Methacrylate-co-Ethylene Dimethacrylate) Rods and Use of the Conjugates as Bioreactors and for Affinity Chromatography*, Biotechnology and Bioengineering, Vol. 49, pp. 355-363 (1996)). Chromatography involving the porous monolith is reportedly based on a precipitation/redissolution phenomenon that separates the polymer according to size—with the precipitated polymer molecules selectively redissolving as the solvent composition is varied. The monolith provides the surface area and permeation properties needed for proper separation.

Another chromatographic separation approach, TREF is a frequently-employed chromatographic technique for differentiating discrete polymer species from polymer blend samples as well as characterizing the components. In TREF, the polymer sample is separated into components according to the solubility of each component in a mobile phase at differing temperatures in solution. More specifically, a polymer sample is injected into a mobile phase of a liquid chromatography system and is passed through a chromatographic column at a low temperature, such as room temperature. The sample precipitates onto the column. The temperature of the column is raised, typically with an oven, and different species of the sample are eluted according to their solubility. Molecules with relatively low degree of solubility in the mobile phase remain in the column for longer periods, and therefore exit the column after molecules with a relatively low degree of solubility. Hence, TREF can characterize one or more separated components of the polymer sample with respect to its crystallinity. A TREF separation typically does not vary mobile phase composition and can be very time consuming. Due to the constraints of heating and equilibrating the system, a typical separation can take up to a day for one sample.

Other separation approaches are also known in the art, including for example, normal-phase adsorption chromatography (with separation of polymer components being based on preferential adsorption between interactive functionalities of repeating units and an adsorbing stationary-phase) and reverse-phase chromatography (with separation of polymer components being based on hydrophobic interactions between a polymer and a non-polar stationary-phase). After separation, a detector can measure a property of the polymer or of a polymer component—from which one or more characterizing properties, such as molecular weight can be determined as a function of time. Specifically, a number of molecular-weight related parameters can be determined, including for example: the weight-average molecular weight ($M_w$), the number-average molecular weight ($M_n$), the molecular-weight distribution shape, and an index of the breadth of the molecular-weight distribution ($M_w/M_n$), known as the polydispersity index (PDI). Other characterizing properties, such as mass, particle size, composition or conversion can likewise be determined.

A variety of continuous-flow detectors have been used for measurements in liquid chromatography systems. Common flow-through detectors include optical detectors such as a differential refractive index detector (RI), an ultraviolet-visible absorbance detector (UV-VIS), or an evaporative mass detector (EMD)—sometimes referred to as an evaporative light scattering detector (ELSD). Additional detection instruments, such as a static-light-scattering detector (SLS), a dynamic-light-scattering detector (DLS), and/or a capillary-viscometric detector (C/V) are likewise known for measurement of properties of interest. Light-scattering methods, both static and dynamic, are established in several areas of polymer analysis. Static light scattering (SLS) can be used to measure $M_w$ and the radii of gyration ($R_g$) of a polymer in a dilute solution of known concentration. Dynamic light scattering (DLS) measures the fluctuations in the scattering signal as a function of time to determine the diffusion constant of dissolved polymer chains or other scattering species in dilute solution or of polymer particles comprising many chains in a heterogeneous system such as dilute emulsion or latex dispersion. The hydrodynamic radius, $R_h$, of the chains or particles can then be calculated based on well-established models.

Presently known liquid chromatography systems are not suitable for efficiently screening larger numbers of polymer samples. Known chromatographic techniques utilizing composition gradients, such as HPLC, can typically take up to an hour or more for each sample to ensure a high degree of separation over the wide range of possible molecular weights (i.e., hydrodynamic volumes) for a sample, while chromatographic techniques utilizing temperature gradients, such as TREF can typically take up to a day or more for each sample to ensure a high degree of separation over the wide range of possible crystallinities for a sample. The known chromatographic techniques can be even longer if the sample is difficult to dissolve or if other problems arise. Also, there are no known systems for effectively utilizing composition and temperature gradients of the mobile phase over a wide range of temperatures and compositions.

Additionally, polymer samples are typically prepared for characterization manually and individually, and some characterization systems require specially-designed sample containers and/or substantial delay-times. For example, optical methods such as light-scattering protocols typically employ detector-specific cuvettes which are manually placed in a proper location in the light-scattering instrument. Such optical protocols can also require a sample to thermally equilibrate for several minutes before measurement. Moreover, because of the nature of many commercial polymers and/or polymer samples—such as their non-polarity and insolubility in water and/or alcohols, their heterogeneous nature, their lack of sequence specificity, among other aspects, the methods, systems and devices developed in connection with the biotechnological, pharmaceutical and clinical-diagnostic arts are generally not instructive for characterizing polymers. Hence, known approaches are not well suited to the rapid characterization of polymers.

Aspects of polymer characterization, such as sample preparation and polymer separation, have been individually and separately investigated. For example, Poché et al. report a system and approach for automated high-temperature dissolution of polymer samples. See Poché et al., *Use of Laboratory Robotics for Gel Permeation Chromatography Sample Preparation: Automation of High-Temperature Polymer Dissolution, J. Appl. Polym. Sci.*, 64(8), 1613-1623 (1997). Stationary-phase media that reduce chromatographic separation times of individual polymer samples have also been reported. See, for example, Petro et al., *Molded continuous poly(styrene-co-divinylbenzene) rod as a separation medium for the very fast separation of polymers; Comparison of the chromatographic properties of the monolithic rod with columns packed with porous and no-porous beads in high-performance liquid chromatography, Journal of Chromatography A*, 752, 59-66 (1996); and Petro et al., *Monodisperse Hydrolyzed Poly(glycidyl methacrylate-co-ethylene dimethacrylate) Beads as a Stationary Phase for Normal-Phase HPLC, Anal. Chem.*, 69, 3131 (1997). However, such approaches have not contemplated nor been incorporated into protocols and systems suitable for large-scale, or even moderate-scale, combinatorial chemistry research, and particularly, for combinatorial material science research directed to the characterization of polymers.

With the development of combinatorial techniques that allow for the parallel synthesis of arrays comprising a vast number of diverse industrially relevant polymeric materials, there is a need for methods and devices and systems to rapidly characterize the properties of the polymer samples that are synthesized.

SUMMARY OF INVENTION

The chromatographic separation system of the present invention allows rapid changes in both temperature and composition of the mobile phase, resulting in rapid separations of polymer samples according to their crystallinity and/or chemical compositions.

The system of the present invention can operate in a variety of separation modes, including: 1) temperature-rising elution fractionation (TREF), which includes running the separation with a strong eluant and raising the temperature from cold to hot, 2) high-temperature, high-performance liquid chromatography (HPLC) system, which includes running the separation at a high temperature and changing the mobile phase composition throughout the separation from a weak eluant to a strong eluant, 3) high-temperature GPC, which includes running a separation at a high temperature with a strong eluant, 4) GPEC (Gradient Polymer Elution Chromatography), which includes low temperature gradient HPLC separations of polymers, 5) low-temperature high-resolution LC, which includes running the separation at room temperature, or colder, while changing the mobile phase composition from a weak eluant to a strong eluant during the separation, 6)room temperature GPC/HPLC, and 7) any combination of those modes, such as a combination of TREF and HPLC by varying both the temperature and the composition of the mobile phase over the course of the separation.

Any of these separation modes can be applied either in an analytical or preparative mode with the system of the invention. An analytical mode is one in which only information regarding the separated components is obtained, whereas a preparative mode is one in which the separation information is obtained as well as separated components are collected as individual samples for further analysis/separation.

These operation modes are accomplished in a variety of ways as is discussed below. Not intending to be limited, these modes include: 1) providing a plurality of mixing zones in a branching fashion (for example a primary zone fed by two secondary mixing zones, fed by three or more tertiary mixing zones, fed by four or more quaternary mixing zones, etc.) in order to mix a variety of different solvents at different temperatures and have separate points of mixing for both compositional and temperature variations, 2) directly coupling the column proximate to the injection valve in order to minimize temperature variations in the mobile phase traveling from the mixing zone through the column and/or to limit the use of tubing, piping or other seperatable fluid connector, thus minimizing parts requirements, 3) integrating the primary mixing zone and the sample injection port into a single injection valve in order to minimize heat loss in the mobile phase and the sample between mixing and injection into and through the column and/or to eliminate the need for additional fluid connections, 4) utilizing a fraction collector either alone or in combination with a detector in order to collect separated sample components for further analysis, and 5) internally heating and cooling the column with the mobile phase; removing the need for an external heating source, such as an oven or heat chamber, and providing a shorter time for achieving desired temperatures in the column.

One application of the invention is as a high throughput screen in a catalyst or polyolefin discovery program as well as a characterization technique for practically any macromolecules that change their solubility within the conditions generated by the techniques.

In one aspect, the invention is a liquid chromatography system which includes a chromatographic column, a detector, an injection port, a fluid distribution system and a control system. The column comprises an inlet port for receiving the mobile phase and the sample, and an effluent port for discharging the mobile phase and separated components of the sample from the chromatographic column. The detector is in fluid communication with the effluent port of the chromatographic column and is used for detecting a property of at least one of the sample components. The injection port is designed for injecting the sample into the mobile phase. The fluid distribution system is designed for varying the composition and the temperature of the mobile phase, and includes a primary mixing zone, a first secondary mixing zone and a second secondary mixing zone. The primary mixing zone is adapted to mix a first primary feed and a second primary feed to form the mobile phase, and is in fluid communication with the inlet port of the chromatographic column. The first secondary mixing zone is adapted to mix a first secondary feed and a second secondary feed to form the first primary feed, and is in fluid communication with the primary mixing zone. The second secondary mixing zone is adapted to mix a third secondary feed and a fourth secondary feed to form the second primary feed, and is in fluid communication with the primary mixing zone. The control system is used for controlling and varying the composition and the temperature of the mobile phase before, during and after the separation, by using one or more control protocols, which include: varying relative flow rates of the secondary feeds supplied to the first secondary mixing zone, varying relative flow rates of the secondary feeds supplied to the second secondary mixing zone, varying relative flow rates of the first primary feed and the second primary feed supplied to the primary mixing zone, and combinations thereof.

In another aspect, the system above further includes a fraction collector. The detector and the fraction collector are in selective fluid communication with the effluent port of the chromatographic column, and the system can further include a valve located between, and in fluid communication with, the effluent port of the column, the detector and the fraction collector. The valve is designed to distribute the flow of the effluent stream from the column to the detector, the fraction collector, or both.

In another aspect, the invention is a liquid chromatography system which includes a first chromatographic column, a second chromatographic column, a detector, a first injection port, a second injection port, a fluid distribution system and a control system. The columns each include an inlet port for receiving a mobile phase and the sample, and an effluent port for discharging the mobile phase and separated components of the sample from the column. The detector is in selective fluid communication with the effluent port of the first and second chromatographic columns, and is used for detecting a property of at least one of the sample components. The first injection port is in selective fluid communication with the inlet port of the first chromatographic column, the second injection port is in selective fluid communication with the inlet port of the second chromatographic column, and both are designed for injecting a sample into the mobile phase. The fluid distribution system is used for controlling and/or varying the composition and temperature of the mobile phase, and includes a first primary mixing zone, a second primary mixing zone, a first secondary mixing zone, a second secondary mixing zone, and a valve. The first primary mixing zone is adapted to mix a first primary feed and a second primary feed to form the mobile phase, and is in fluid communication with the inlet port of the first chromatographic column. The second primary mixing zone is adapted to mix the first primary feed and the second primary feed to form the mobile phase, and is in fluid communication with the inlet port of the second chromatographic column. The first secondary mixing zone is adapted to mix a first secondary feed and a second secondary feed to form the first primary feed, and is in selective fluid communication with the first and second primary mixing zones. The second secondary mixing zone is adapted to mix a third secondary feed and a fourth secondary feed to form the second primary feed, and is in selective fluid communication with the first and second primary mixing zones. The valve is located between and in fluid communication with the first and second secondary mixing zones and the first and second primary mixing zones, and is adapted to direct the flow of the first and second primary feeds from the first and second secondary mixing zones to the first primary mixing zone, the second primary mixing zone, or both. The control system is used for controlling the composition and the temperature of the mobile phase by using one or more control protocols including: varying relative flow rates of the secondary feeds supplied to the first secondary mixing zone, varying relative flow rates of the secondary feeds supplied to the second secondary mixing zone, varying relative flow rates of the first primary feed and the second primary feed supplied to the first primary mixing zone, varying relative flow rates of the first primary feed and the second primary feed supplied to the second primary mixing zone, and combinations thereof.

In another aspect, the invention is a liquid chromatography system which includes a chromatographic column, a detector, an injection valve and a control system. The column includes an inlet port for receiving a mobile phase and the sample, and an effluent port for discharging the mobile phase and separated components of the sample from the column. The detector is in communication with the effluent port of the chromatographic column, and is used for detecting a property of at least one of the sample components. The injection valve is proximately coupled to the inlet port of the chromatographic column, and is used for injecting the sample with the mobile phase into the chromatographic column. The injection valve includes a primary mixing zone adapted to mix a first primary feed and a second primary feed to form the mobile phase, an injection port adapted for injecting the sample into the injection valve, and an outlet adapted for providing a flow path from the injection valve to the chromatographic column, wherein the outlet of the injection valve and the inlet port of the chromatographic column are proximately coupled. The control system is designed and used for controlling the temperature or the composition of the mobile phase in the system by varying relative flow rates of the first primary feed and the second primary feed supplied to the primary mixing zone.

In another aspect, the system above further includes a fraction collector. The detector and the fraction collector are in selective fluid communication with the effluent port of the chromatographic column, and the system can further include a valve located between, and in fluid communication with, the effluent port of the column, the detector and the fraction collector. The valve is designed to distribute the flow of the effluent stream from the column to the detector, the fraction collector, or both.

In yet another aspect, the invention is a liquid chromatography system which includes a first chromatographic column, a second chromatography column, a detector, a first injection valve, a second injection valve and distribution valve and a control system. The columns each include an inlet port for receiving a mobile phase and the sample, and an effluent port for discharging the mobile phase and separated components of the sample from the chromatographic column. The detector in selective fluid communication with the effluent ports of the first and second chromatographic columns, and is used for detecting a property of at least one of the sample components. The first and second injection valves are proximately coupled to the inlet ports of the first and second chromatographic columns respectively, and are used for injecting the sample with the mobile phase into the first or second chromatographic columns. The injection valves each include a primary mixing zone adapted to mix a first primary feed and a second primary feed to form the mobile phase, an injection port adapted for injecting the sample into the injection valve, and an outlet adapted for providing a flow path from the injection valve to the chromatographic column, wherein the outlet of the injection valve and the inlet port of the chromatographic column are proximately coupled. The distribution valve is located between and is in fluid communication with the first and second injection valves, and is adapted to direct the flow of the first and second primary feeds to the primary mixing zone in the first injection valve, the primary mixing zone in the second injection valve, or both. The control system is designed and used for controlling the temperature or the composition of the mobile phase by varying relative flow rates of one or more of the feeds supplied to the primary mixing zones.

In yet another aspect, the invention is a liquid chromatography system which includes a chromatographic column, a fraction collector, an injection port, a mixing zone, a first line maintained at a first temperature for delivering a primary feed to the mixing zone, a second line maintained at a second temperature different from the first temperature for delivering a second primary feed to the mixing zone and a control system. The column includes an inlet port for receiving a mobile phase and the sample, and an effluent port for discharging the mobile phase and separated components of the sample from the column. The fraction collector is in fluid communication with the effluent port of the chromatographic column, and is used for collecting the separated components of the sample in separate vessels. The injection port is in selective fluid communication with the inlet port of the chromatographic column, and is used for injecting the sample into the mobile phase. The mixing zone is adaptable for mixing a first primary feed and a second primary feed to form the mobile phase, and is in fluid communication with the inlet port of the chromatographic column. The control system is designed and used for controlling the composition and the temperature of the mobile phase by using one or more control protocols, including: varying relative flow rates of one or more of the feeds, varying the temperatures of the first and second lines, and combinations thereof. In one aspect the first line is electrically heated, and the second line is chilled.

In yet another aspect, the invention is a liquid chromatography system which includes a first chromatographic column, a second chromatographic column, a fraction collector, first and second injection ports, first and second fluid distribution systems, a valve and a control system. The columns each include an inlet port for receiving a mobile phase and the sample, and an effluent port for discharging the mobile phase and separated components of the sample from the column. The fraction collector is in selective fluid communication with the effluent ports of the first and second chromatographic columns, and is used for collecting the separated components of the sample in separate vessels. The injection ports are in selective fluid communication with the inlet ports of the chromatographic columns, and are used for injecting the sample into the mobile phase. The first fluid distribution system includes a first mixing zone in fluid communication with the inlet port of the first chromatographic column for mixing a first primary feed and a second primary feed to form the mobile phase, a first line maintained at a first temperature, for delivering the first primary feed to the mixing zone, and a second line maintained at a second temperature different from the first temperature, for delivering the second primary feed to the mixing zone. The second fluid distribution system includes a second mixing zone in fluid communication with the inlet port of the second chromatographic column, adaptable for mixing the first primary feed and the second primary feed to form the mobile phase, a third line maintained at a third temperature, for delivering the first primary feed to the third mixing zone, and a fourth line maintained at a fourth temperature different from the third temperature, for delivering the second primary feed to the second mixing zone. The valve is located between and in fluid communication with the first and second mixing zones, and is adapted to direct the first and second primary feed to the first mixing zone, the second mixing zone, or both. The control system is designed and used for controlling the composition and the temperature of the mobile phase by using one or more control protocols, including: varying relative flow rates of the first primary feed and the second primary feed supplied to the first mixing zone, varying relative flow rates of the first primary feed and the second primary feed supplied to the second mixing zone, varying the temperatures of the first, second, third and fourth lines, and combinations thereof.

In yet another aspect, the invention is a liquid chromatography system which includes a chromatographic column, a detector, an injection port, a mixing zone and a control system. The column is located in an ambient temperature environment, and includes an inlet port for receiving a mobile phase and the sample, and an effluent port for discharging the mobile phase and separated components of the sample from the chromatographic column. The chromatographic column is adapted to be heated or cooled internally by the mobile phase in the absence of any heating chamber. The detector is in fluid communication with the effluent port of the chromatographic column and is used for detecting a property of at least one of the sample components. The injection port is in selective fluid communication with the inlet port of the chromatographic column and is used for injecting the sample into the mobile phase. The mixing zone is adapted to mix a first primary feed and a second primary feed to form the mobile phase. The control system is designed and used for controlling a composition and a temperature of the mobile phase by varying the relative flow rates of one or more of the feeds.

In yet another aspect, the invention is a separation unit, which includes an injection valve and a chromatographic column. The column includes an inlet port for receiving a mobile phase and the sample, and an effluent port for discharging the mobile phase and separated components of the sample from the column. The injection valve is proximately coupled to the inlet port of the chromatographic column, and is used for injecting the sample with the mobile phase into the chromatographic column. The injection valve includes a mobile phase inlet for introducing one or more feeds into the injection valve. If there are more than one feed, the injection valve also includes a mixing zone adapted to mix a first feed and a second feed to form the mobile phase. The injection valve also includes an injection port adapted for injecting the sample into the injection valve, and an outlet adapted for providing a flow path from the injection valve to the chromatographic column. The outlet of the injection valve and the inlet port of the chromatographic column are proximately coupled.

In yet another aspect, the invention is a method for characterizing a sample, which includes creating a mobile phase, controlling a temperature of the column, injecting the sample into the mobile phase, delivering the sample and the mobile phase through a chromatography column, separating one or more sample components of the sample in the chromatography column while varying the temperature and the composition of the mobile phase, detecting a property of the separated components of the sample, and collecting the separated components of the sample in separate vessels of a fraction collector. The mobile phase is created by a method that includes supplying a first primary feed to a primary mixing zone via a heated line maintained at a first temperature, supplying a second primary feed to the primary mixing zone via a chilled line maintained at a second temperature different than the first temperature, and mixing the first and second primary feeds to create the mobile phase.

In yet another aspect, the invention is a method for characterizing a sample, which includes creating a mobile phase, controlling a temperature and a composition of the mobile phase, injecting the sample into the mobile phase, delivering the mobile phase and the sample through a chromatography column, separating one or more sample components of the sample in the chromatography column while varying the temperature and composition of the mobile phase, and detecting a property of the separated components of the sample. The mobile phase is created by: creating a first primary feed by supplying a first secondary feed and a second secondary feed to a first secondary mixing zone, creating a second primary feed by supplying a third secondary feed and a fourth secondary feed to a second secondary mixing zone, supplying the first primary feed from the first secondary mixing zone to a primary mixing zone via a first line maintained at a first temperature, supplying the second primary feed from the second secondary mixing zone to the primary mixing zone via a second line maintained at a second temperature different than the first temperature, and mixing the first and second primary feeds in the primary mixing zone to form the mobile phase. The temperature and composition of the mobile phase are controlled with a control system by using one or more control protocols including: varying relative flow rates of the secondary feeds supplied to the first secondary mixing zone, varying relative flow rates of the secondary feeds and supplied to the second secondary mixing zone, varying relative flow rates of the first primary feed and the second primary feed supplied to the primary mixing zone, and combinations thereof.

In another aspect, the systems and methods described above are automated.

Other features, objects and advantages of the present invention will be in part apparent to those skilled in art and in part pointed out hereinafter. All references cited in the instant specification are incorporated by reference for all purposes.

Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIGS. 2A and 2B are schematic representations of a multi-port injection valve in a first and second position for use in the liquid chromatography system the present invention.

FIGS. 6A through 6D are graphical data showing the attainable temperature controls for the environments in the columns of the liquid chromatography system of the present invention by controlling line temperatures, flow rates of solvents and compositional control of solvent mixtures. FIG. 6A is a plot showing the temperature of the mobile phase at the inlet of the column after fifteen minutes. The plot shows temperature monitored at the inlet of the column versus the temperature of the heated line for various flow rates. FIG. 6B is a plot showing the temperature of the mobile phase at the outlet of the column after fifteen minutes. The plot shows temperature monitored at the outlet of the column versus the temperature of the heated line for various flow rates. FIG. 6C is a plot showing the temperature of the mobile phase at the outlet of the column after twenty minutes. The plot shows temperature monitored at the outlet of the column versus the percentage of heated mobile phase fluid in the mobile phase for various flow rates with the heated line set at 280 C. and the chilled line set at −16 C. FIG. 6D is a plot showing the monitored temperature versus the mobile phase eluant flow rate for various eluant compositions at both the inlet and the outlet of the column, with the heated line set at 280 C. and the chilled line set at −16 C.

FIG. 8 is a chromatogram of the TREF and HPLC separation analysis of the blend of Samples X, Y and Z as described in the Examples.

DETAILED DESCRIPTION OF THE INVENTION

Figure 1:
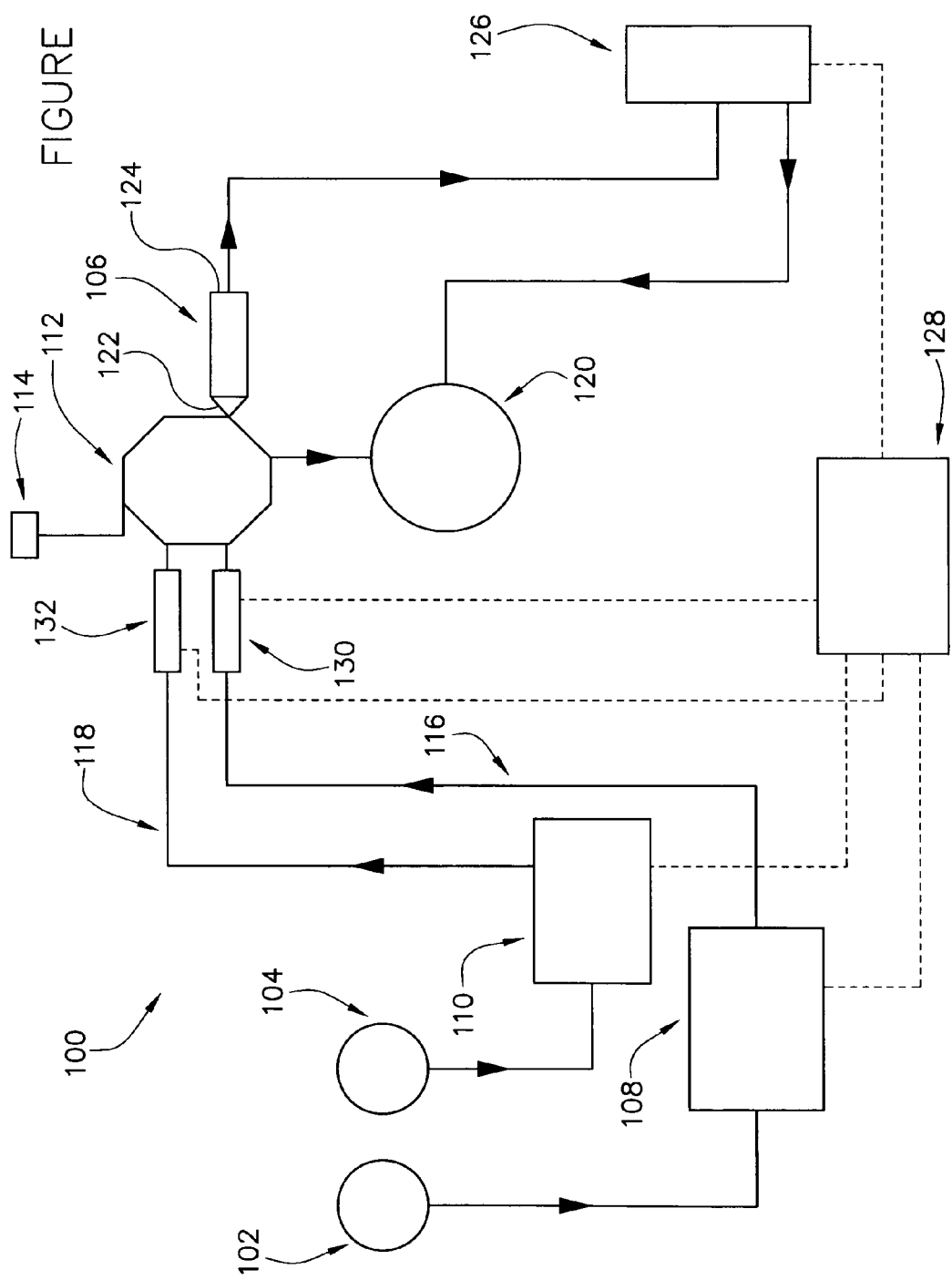
FIG. 1 is a schematic representation of one embodiment of a liquid chromatography system of the present invention.

Certain characterizing features of this invention are related to inventions described in U.S. Pat. Nos. 6,175,409, 6,260,407, 6,265,226, 6,294,388, 6,296,771, 6,345,528, 6,406,632, 6,492,184, and 6,730,228. Each of the aforementioned U.S. patents are hereby incorporated by reference for all purposes.

In the present invention, methods and apparatus are disclosed for characterization of single polymer samples and/or for characterization of a library comprising four or more polymer samples. Preferably, the characterization methods and apparatus can be applied for fingerprinting biological and non-biological polymer samples—for analysis in an analytical laboratory, or for analysis in an on-line, near real time process monitoring or process control system.

In the present invention, methods and apparatus having features that enable an effective combinatorial polymer research program are provided. Such a research program may be directed, for example, to identifying or optimizing commercially valuable polymers, catalysts or other materials, or to other research goals, such as process characterization and optimization. Other applications, including industrial process monitoring or control are also enabled by the present invention.

With respect to automated polymer sampling, for example, a plurality of polymer samples can be loaded into a liquid chromatography system using an auto-sampler having a very high sampling rate—less than 10 seconds per sample, or in some embodiments, less than 5 seconds per sample. Additionally, automated sample preparation can be effected in a direct rapid-serial manner (i.e., serial sample withdrawal-preparation-loading). The plurality of samples can be loaded, moreover, into multiple injection valves which are supplied by common fluid reservoirs, the injection valves having similar separation conditions, such as composition and temperature of the mobile phase, or different conditions—thereby providing a load-load capability wherein a second sample can be loaded while the first sample is being injected into the characterization system.

With respect to chromatographic separation, a number of techniques can be employed to efficiently and effectively separate one or more of the various components of a heterogeneous polymer sample from one or more other components thereof. For example, the column geometry, preferably in combination with the separation medium, can be optimized to obtain the desired throughput and/or minimize heat loss. Preferred column geometries include relatively short, high-aspect ratio columns (as compared to conventional columns). Preferred separation media include a stationary phase selected for targeted separation ranges—for example, to quickly pass a high molecular-weight fraction of a sample (e.g., >about 1000 D) while retaining a low molecular-weight fraction of the sample. Other separation medium optimization approaches, such as combining size-exclusion chromatography (SEC) with an adsorption chromatography, are also preferred in some applications. The mobile phase of a liquid chromatography system can also be controlled to improve sample-throughput. For example, mobile phase compositional gradients, mobile phase temperature gradients or mobile phase flow rate gradients can be employed individually or collectively, and the time-rate of change of such gradients can affect separation performance. For some applications, solvent selection can itself be optimized to improve the efficiency of loading and/or eluting the sample or components thereof onto/from the stationary phase.

In one embodiment, the present invention is preferably suitable for precipitation-redissolution chromatography, which involves the use of mobile phase having a solvent gradient in conjunction with an insoluble stationary-phase (e.g., a polymer monolith). The polymer sample is injected into a mobile phase solvent that is a "poor" solvent for the polymer being characterized (sometimes called a "non-solvent"), thereby causing precipitation of the polymer sample. The precipitated polymer sample then adsorbs onto the stationary-phase (e.g., monolith) surface. Gradually, a better solvent for the polymer being characterized is introduced into the mobile phase. When the better solvent contacts the precipitated polymer sample, the smaller particles of the polymer sample redissolve first. As more of the better solvent contacts the precipitated polymer sample, larger particles of the polymer sample redissolve, until the entire polymer sample has been redissolved. In this fashion, the polymer sample is separated by size (with the smaller particles corresponding to smaller size molecules). Solvent choices depend on the solubility characteristics of the polymer samples being characterized. For a typical hydrophobic polymer such as polystyrene, "good" solvents include tetrahydrofuran, toluene, dichloromethane, trichlorobenzene, dichlorobenzene, cyclohexane, etc., while "poor" non-solvents include methanol, ethanol, water, or hexane. It is generally preferred that the good solvent and the poor solvent used for any particular separation be miscible.

The speed of separation of the precipitation-redissolution chromatographic techniques depends on the gradient profiles (e.g., the time rate of change of the mobile phase composition13 between solvent and non-solvent). Typical pump systems supplied by HPLC equipment manufacturers have sufficient speed and accuracy such that the rate of introduction of the better solvent can be controlled to effectively elute the precipitated polymer sample in about 1 minute or less, and in some cases, less than about 45 seconds. Flow rates of the mobile phase are preferably about 5 mL per minute and higher, up to the limit of the pump system used, which can be 20-40 mL per minute for commercial pumps with large-volume pump heads.

Since polymer solubility is also a function of temperature, temperature gradients can also be employed, individually or in combination with the mobile phase compositional (e.g., solvent) gradient. The temperature-gradient technique can also have applications at relatively low temperatures—near ambient or below, depending on the particular polymer samples being characterized.

Briefly, the sample is introduced at a lower temperature, enhancing precipitation of the polymer, and then the temperature is increased (optionally in conjunction with a change in composition of the mobile phase to a good solvent) to allow selective dissolution and elution of retained polymer.

The precipitation-redissolution chromatography approaches described herein—particularly employing monolithic columns such as those disclosed by Petro et al., vide supra., generally lead to high-speed characterization with good quality of information.

For the liquid chromatography systems, the flow-rate of the mobile phase can be increased substantially (e.g., by a factor of ten or more) relative to conventional flow characterization systems. The mobile phase flow rates can also be temporally varied as a sample moves through the system—for example, with relatively high flow rates to advance the sample to a detector, and relatively slow flow rates to detect a property of the sample or of a component thereof.

With respect to detection, a low-molecular weight insensitive mass detector, such as an evaporative light-scattering detector (ELSD) can be advantageously employed in liquid chromatography approaches in cooperation with overlaid sample injection approaches. Specifically, trailing-edge components from a preceding sample and leading-edge components from a succeeding sample can reside in a detection cavity simultaneously, without compromising relevant data collection. In addition, rapid, indirect calibration standards and methods impact overall system speed.

Several important aspects of the invention have direct implications for high-temperature characterization efforts (typically ranging from about 75° C. to about 225° C.). With regard to polymer sampling, for example, a directly heated auto-sampler probe can be employed. With respect to chromatographic separation, mobile phase temperature and composition gradients can be employed and controlled for temperatures varying from about −50° C. to about 300° C. Finally, detectors that are less-sensitive to variations in temperature, as compared with typical high-temperature characterization detectors, offer a greater degree of freedom for system configuration at reduced costs.

These and other aspects of the invention are to be considered exemplary and non-limiting, and are discussed in greater detail below. The several aspects of the polymer characterization methods and systems disclosed and claimed herein can be advantageously employed separately, or in combination to efficiently characterize polymeric materials. In preferred embodiments, these features are employed in combination to form a polymer characterization system that can operate as a high-throughput screen in a materials science research program directed to identifying and optimizing new polymers, new catalysts, new polymerization reaction conditions and/or new post-synthesis processing conditions. Certain characterizing information—particularly molecular weight, molecular weight distribution, crystallinity, composition and conversion information—are broadly useful for characterizing polymers and polymerization reactions. As such, the particular polymers and/or mechanisms disclosed herein should be considered exemplary of the invention and non-limiting as to the scope of the invention.

The invention is described in further detail below with reference to the figures, in which like items are numbered the same in the several figures.

Referring to FIG. 1, in one embodiment, the liquid chromatography system 100 comprises a plurality of reservoirs 102 104 containing a plurality of fluids in fluid communication with a liquid chromatography column 106. A first pump 108 provides communication between the first fluid reservoir 102 and the column 106 for continuously supplying a feed from the reservoir 102 through the column 106. A second pump 110 provides fluid communication between the second fluid reservoir 104 and the column 106 for continuously supplying a feed from the reservoir 104 through the column 106. The liquid chromatography system 100 further includes an injection valve 112, that can include an injection port 114 for receiving samples from a sample source (e.g., such as a sample handling robot, or from an on-line sampling system in a polymerization process line, not shown). The injection valve 112 is in fluid communication with the fluid reservoirs 102 104 via a chilled line 116 and a heated line 118, provides a mixing zone (shown in FIGS. 2A and 2B) for the feeds to form a mobile phase, and is adapted for serially injecting polymer samples into the mobile phase. The mixing of feeds to form the mobile phase inside the injection valve, as opposed to external mixing points situated prior to the injector or point of injection allows for improved temperature control of the mobile phase and therefore, improved separation control and time. The liquid chromatography system can further include a flow-through detector 126 in fluid communication with an effluent port 124 of the chromatographic column 106 for detecting a property of at least one of the sample components. The liquid chromatography system can also include a control system 128 for controlling the temperature and/or the composition of the mobile phase in the mixing zone by varying the relative flow rates of the feeds supplied to the mixing zone from the reservoirs and controlling the temperatures of the lines 116 118. Finally, a waste area 120 is also included and can be in fluid communication with the injection valve 112 and/or the detector 126.

In general, the column 106 comprises a stationary-phase within a separation cavity, an inlet port 122 adapted to receive the mobile phase from the injection valve 112 and for supplying the sample to the separation cavity, and an effluent port 124 for discharging the mobile phase and the polymer sample or separated components thereof from the separation cavity. The column may be constructed of a material that can withstand high temperatures (up to 280 C.) while minimizing heat loss from the system. One such type of material is polyether ether ketone (PEEK) or high temperature polyether ether ketone (HTPEEK) (American Industrial Plastics, Daytona Beach, Fla.). While PEEK material allows for higher temperatures with minimal heat loss, it can become weak from excessive heating and cooling. Thus, in one embodiment, a combination of metal and PEEK materials can be used for the column, with the metal being useful for connectors and lines. The column preferably has a length between about 2 cm and about 15 cm, and a column inner diameter between about 2 mm to about 25 mm.

Figure 1A:
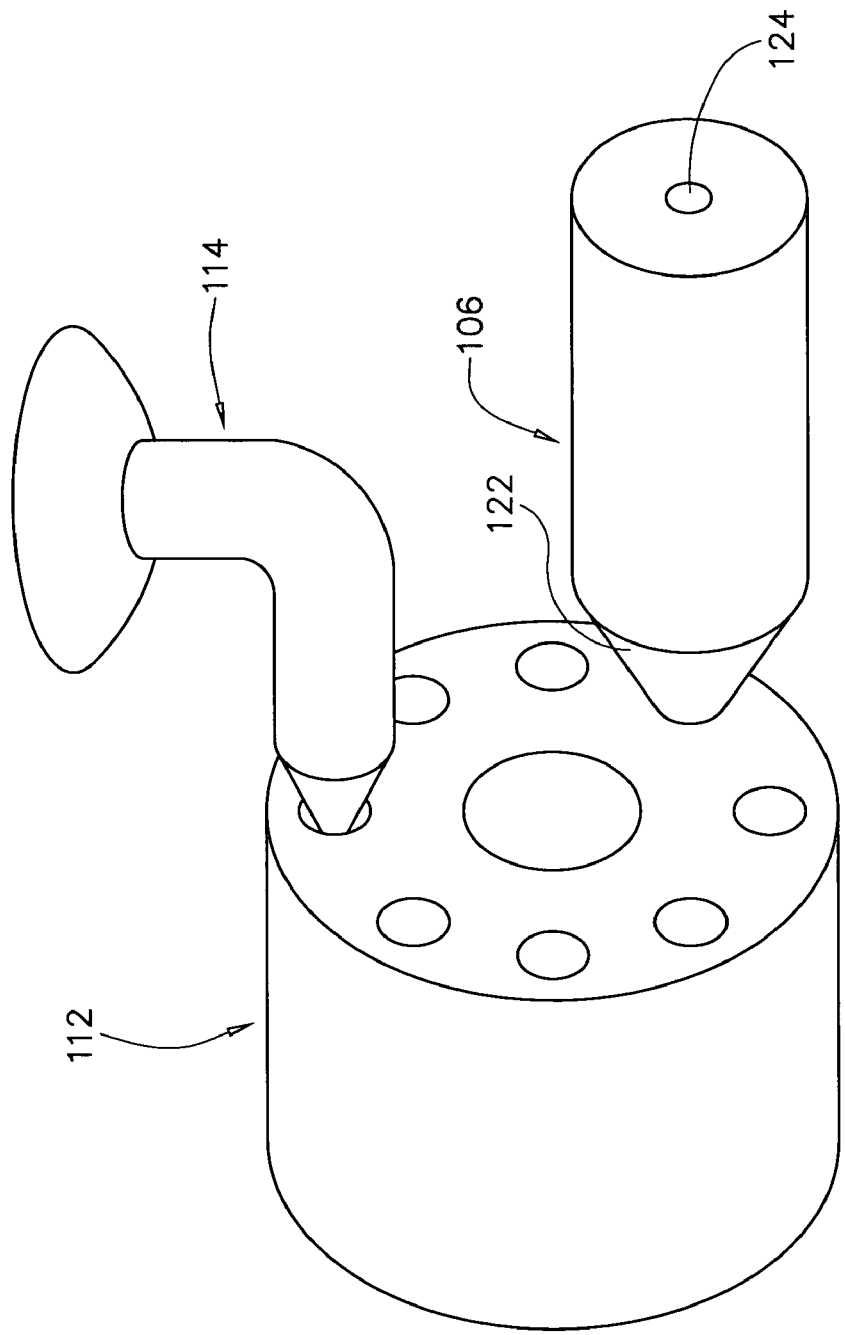
FIG. 1A is a perspective view of a chromatographic column proximately coupled to an injection valve.

In one embodiment, the injection valve 112 is proximately coupled with the inlet port 122 of the chromatographic column 106, such as is depicted in FIG. 1A. By proximately coupled, it is meant that the inlet of the column and the outlet of the injection valve are connected in a mating relationship such that the inlet of the column and the outlet of the injection valve are located adjacent to each other. This design minimizes connection volumes and parts and provides better control of the temperature of the internal environment of the column by providing a shorter path for the mobile phase and reducing the amount of heat loss/gain. In some embodiments, the column 106 is entirely or substantially heated and cooled internally by the mobile phase. In these embodiments no heating chamber is utilized, and it is beneficial to reduce areas that can subject the mobile phase to heat loss. In other embodiments, the column is located in a heat chamber, such as an oven (not shown), the injection valve is located outside of the heat chamber, and the column and injection valve are in fluid communication via a delivery line.

Heating and chilling the delivery lines 116 118 allows for a fast, controlled method of heating and chilling the feeds before they are mixed. By controlling the flow rates of the feeds and the temperatures of the lines, the temperature of the mobile phase can be ramped up to high temperatures, or cooled to low temperatures very quickly. This results in an ability to quickly heat or cool the column, thus obtaining a separation across a wide temperature gradient over a short period of time. Significantly, system comprises a first 130 and second 132 temperature-control element in thermal communication with the first and second delivery lines 116 118 for maintaining the line temperatures at a predetermined temperature or within a predetermined range of temperatures and heating or cooling the feeds to a predetermined temperature or within a predetermined range of temperatures. The temperature-control elements 130 132 can be, in the general case, a heating element or a cooling element. The particular design of the heating element or cooling element is not critical. In one embodiment, the heating element can be, for example, a resistive-heating element such as a resistive wire in adjacent proximity to the line 118. The heating element can alternatively be a fluid-type heat-exchanger heating element having a fluid-containing tubular coil around the line. In any case, the temperature-controlled lines can have a body encasing the heating element, and preferably a thermocouple for temperature monitoring and control. In one embodiment, the first temperature control element 130 is a metal capillary line that is located coaxially inside a tube with re-circulated chilling fluid, and the second temperature control element 132 is an electrically heated metal capillary line. The heated line 118 is maintained at a temperature of between about 70° C. and 300° C., more specifically between about 100° C. and 300° C., more specifically between about 150° C. and 300° C., more specifically between about 220° C. and 280° C., and more specifically between about 250° C. and 280° C. The chilled line 116 is maintained at a temperature of between about −60° C. and 10° C., more specifically between about −30° C. and 0° C., and more specifically between about −20° C. and 0° C.

Figure 3:
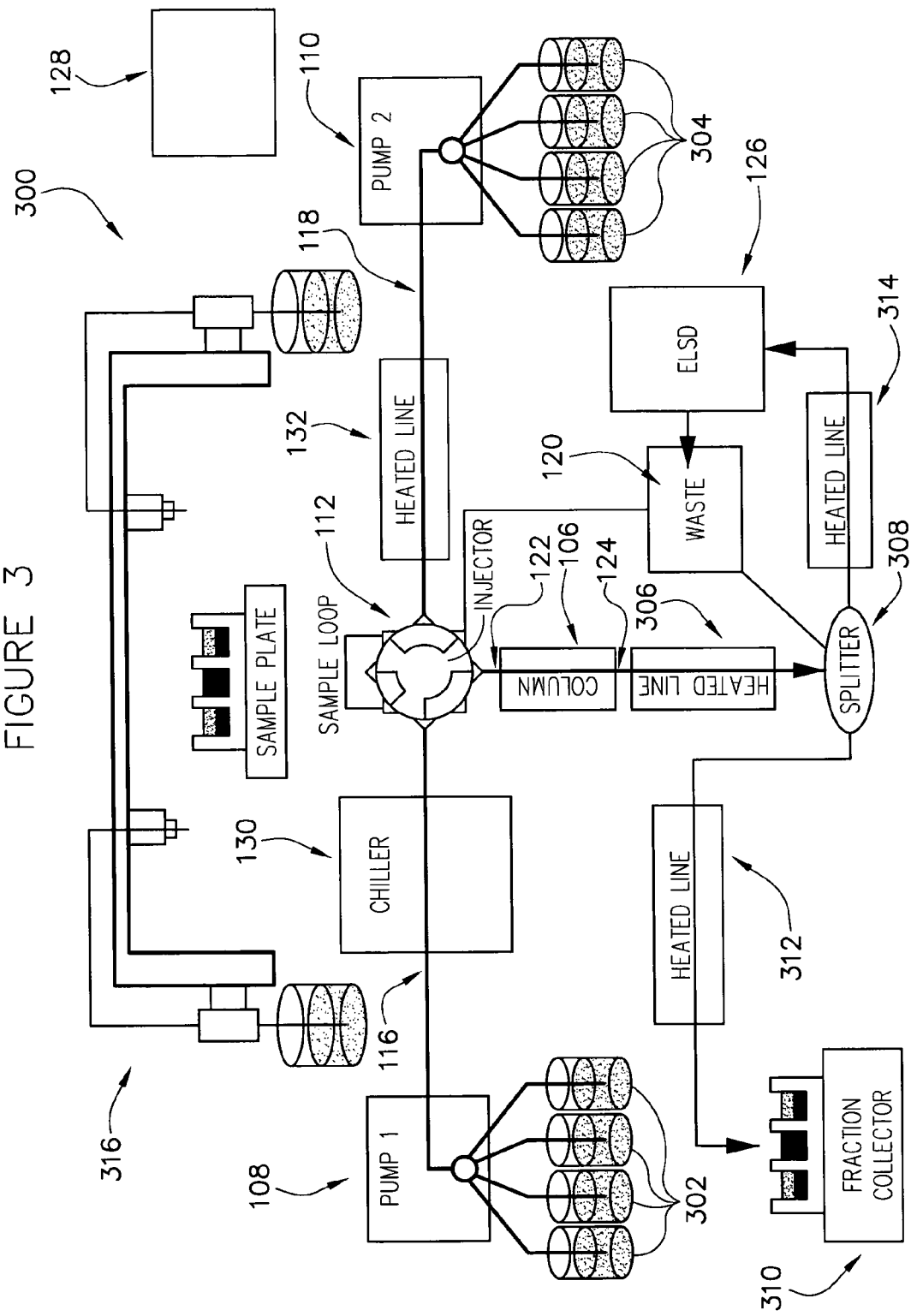
FIG. 3 is a schematic representation of another embodiment of a liquid chromatography system of the present invention.

The reservoirs 102 104 can be of any suitable design and capacity, and typically has a volume of about 4 liters. The particular mobile phase fluid to be included in the reservoir 102 for the flow characterization system can be selected in view of the polymer sample, detector, desired flow rates, and liquid chromatography systems, further in view of the chromatographic separation technique being employed. Exemplary mobile phase fluids for liquid chromatography systems (e.g., GPC, precipitation-redissolution chromatography, adsorption chromatography and reverse-phase chromatography) include those fluids that are typically strong eluants, such as trichlorobenzene, toluene, tetrahydrofuran, etc., those fluids that are typically weak eluants, such as water, methanol, ethanol, etc., as well as more volatile solvents, such as pentane, methanol, acetone, tetrahydrofuran, etc., that can be added to the mobile phase to improve detectablility when using a detector such as an ELSD. The flow characterization systems can include additional reservoirs as depicted in FIG. 3 as 302 and 304 to provide more than one mobile phase fluid, to provide a mobile phase composition gradient or, as discussed below, to provide a mobile phase temperature gradient.

As depicted in FIG. 1, a control system 128 including one or more microprocessors can, as noted above, be employed for controlling every aspect of the flow characterization systems, including: the pumps 108 110 (e.g., mobile phase flow-rate, flow-rate gradients, compositional gradients, temperature gradients, acceleration rates for such gradients); the reservoirs 102 104 (e.g., temperature, level); the auto-sampler 316 (FIG. 3) (e.g., movements between spatial position, timing thereof, sample selection, sample preparation, sampling pump flow-rates, and other operations), the injection valve 112 (e.g., timing, selection of sample loops, etc.); the column 106 (e.g., column selection (if multiple columns and automated column-switching valves are present), column temperature); the detector 126 (e.g., data acquisition (e.g., sampling rate), data processing (e.g., correlation); the detector parameters (e.g., wavelength); the fraction collector 310 (FIG. 3) and/or overall system conditions (e.g., system pressure, temperature). Software is typically available from detector and/or liquid chromatography system manufacturers (e.g., MILLENIUM™ 2000 software available from Waters (Milford, Mass.).

Referring now to FIGS. 2A and 2B, in many embodiments, the injection valve 112 shown in FIG. 1 can be a multi-port injection valve 200, preferably comprising a sample loop 202, which can be internal or external. In some embodiments, the injection valve 200 is an injection port valve typical of those used for a high-pressure liquid chromatography system. As used in this context, "high pressure" refers to internal system pressures (e.g., mobile phase pressures) above atmospheric pressure, typically ranging from about 0 psig to about 6000 psig, preferably from about 10 psig to about 4000 psig, and more typically from about 100 psig to about 2000 psig.

In a first switch position and valve configuration depicted in FIG. 2A, the incoming heated and chilled feeds are fed into two separate inlet ports 204 206 of the injection valve 200. The feeds combine in a channel 208 (which is the mixing zone, also called a primary mixing zone in the presence of secondary mixing zones) to form the mobile phase. The first switch position and valve configuration allows for the feeds to mix to form the mobile phase and to be routed through an outlet 210 to the column as depicted by arrows in the flow path. Meanwhile, the sample is injected or fed into a separate inlet port 212 of the injection valve 200 at relatively low pressure compared to the pressure of the mobile phase. The injection port 212 can be adapted in size to accommodate one or more injection probes (tips) of a manual or an automated sample delivery unit (e.g., an auto-sampler). The first switch position and valve configuration allows for the sample to pass through an inlet 214 of the sample loop 202, through the sample loop 202, and through an outlet 216 thereof to a waste outlet 218, thereby loading the sample.

When the switch position and valve configuration is switched to an alternative second switch position and valve configuration, as depicted in FIG. 2B, the inlet 214 of the sample loop 202 is aligned with the mobile phase coming from the mixing zone 208, and the outlet of the sample loop 216 is aligned for fluid communication with an outlet 210 to the column such that a discrete volume of the sample equal to the volume of the sample loop 202 is injected into the mobile phase and through the column. Repeated alternation between the first and second switch positions/valve configurations allows for injecting of corresponding discrete sample volumes into the mobile phase.

Injection valves, such as represented in FIGS. 2A and 2B, can be purchased as eight port injection valves from Valco Instruments Co. Inc. (Houston, Tex.), and the purchased valve fittings can be modified as described above for use in connection with a liquid chromatography system. For example, in the embodiment shown in FIGS. 2A and 2B, an eight port injection valve can be used with one of the ports 220 being plugged to essentially create a seven port injection valve. While the eight-port valve 200 depicted schematically in FIGS. 2A is a preferred configuration, other high-pressure injection valves can also be suitably employed, including, without limitation, valves having a greater or lesser number of ports. Typically, however, a high-pressure injection valve will have from 6 to 24 ports.

Depending on the sample size required (such as for an analytical separation, which can use around 2 mL of sample versus a preparative separation—a separation where fractions are collected for further analysis—which can require around 5 mL of sample), the sample loop can be located internally or externally. In the case of larger samples, such as in some preparative applications, an internal sample loop may not have a large enough volume, necessitating the need for an external sample loop. An external sample loop creates the issue of greater heat loss of the sample. Various approaches can be employed in order to minimize the heat loss. In one embodiment, the sample loop can be a stainless steel capillary that is actively heated. In another embodiment, the external sample loop can be constructed of a material that has a low thermal conductivity and can be thermally isolated. One such material is PEEK or High temperature PEEK.

Other types of injection valves can be used, including for example, arrays of microvalves configured for sampling and injection, for example, analogous to that described in U.S. Pat. No. 6,742,544 entitled "Gas Chromatograph Injection Valve Having Microvalve Array", which is hereby incorporated by reference for all purposes.

FIG. 3 shows another embodiment of a liquid chromatography system of the present invention, similar to the embodiment shown in FIG. 1, with additional features. In this embodiment, the liquid chromatography system 300 additionally includes at least four reservoirs 302 in fluid communication with the pump 108 and chilled line 116, and at least four reservoirs 304 in fluid communication with the pump 110 and heated line 118. The embodiment further includes a fraction collector 310 in selective fluid communication with the effluent port of the column 124, and a valve 308, such as a splitter, located between the column 106 and the detector 126, and the fraction collector 310. The valve 308 is designed to direct flow of the effluent from the column 106, to a fraction collector 310, or both. In addition, the line 306 providing fluid communication between the valve 308 and the column 106 as well as the lines 312 314 that deliver fluids to the fraction collector 310 and detector 126 can be optionally heated or cooled by various methods or devices such as those methods and devices used to heat or chill the lines 116 and 118. The embodiment further includes an optional sample preparation and delivery station 316, which can be automated.

In one embodiment, each reservoir contains a different solvent or fluid. In other embodiments the four solvents or fluids contained in one set of reservoirs 302 are different from each other, and are the same solvents or fluids contained in the other set of reservoirs 304. The embodiment disclosed in FIG. 3 provides a plurality of secondary mixing zones located within the pumps 108, 110. The pumps can be purchased as quaternary pumps available from Agilent Technologies (Palo Alto, Calif.). The pumps 108 110 receive and mix the incoming feed streams (also called secondary feed streams) from the reservoirs 302 304 at low pressure, such as atmospheric pressure, and send out a feed stream to the injection valve 112 at high pressure. As discussed above, "high pressure" refers to internal system pressures (e.g., mobile phase pressures) above atmospheric pressure, typically ranging from about 0 psig to about 6000 psig, preferably from about 10 psig to about 4000 psig, and more typically from about 100 psig to about 2000 psig. The pumps 108 110 act as secondary mixing zones, which act to combine the secondary feed streams supplied from the reservoirs 302 304 and create two primary feed streams which combine in the primary mixing zone, such as in the injection valve 112, to create the mobile phase. The pumps 108 110 can vary the flow rates of the various feeds in the system between about 0.1 to about 40 mL/minute, with a preferred flow rate range of 2-5 mL/minute for analytical separations, and 5-20 mL/minute for preparative separations.

In one embodiment, the secondary mixing zones 108 110 provide a first dimension compositional mixing (by mixing the plurality of fluids provided by the reservoirs 302 304), and the primary zone provides a second dimension compositional mixing (by mixing the mobile phase fluids provided by the secondary mixing zones 108 110) as well as a temperature mixing (the mobile phase fluids being delivered at different temperatures due to the heated 118 and chilled 116 lines). In another embodiment, the reservoirs 302 304 are also maintained at temperatures above or below ambient conditions, and the secondary mixing zones 108 110 can provide temperature mixing as well as compositional mixing.

The fraction collector 310 provides the ability to collect fractions of the separated sample into separate vessels. The vessels are fed by an outlet of the feed line to the fraction collector 310. In one embodiment, the outlet is a needle coupled to the feed line. In one embodiment, the outlet is stationary, and the fraction collector 310 is an array of vials located on a platform or carousel that is translatable or rotatable and can be controlled by the control system 128 to change the vessel being fed from the outlet. In another embodiment, the outlet is translatable from one vessel to another, while the fraction collector 310 remains stationary. Fraction collectors are well known in the art, such as that disclosed in U.S. Pat. No. 6,562,232 to Myogadani, the disclosure of which is hereby incorporated by reference.

The valve 308 can be designed to direct flow to either the detector 126 or the fraction collector 310, or can split the flow allowing a certain amount of the effluent to flow to the detector and a certain amount to flow to the fraction collector 310. This can be advantageous for real time monitoring of sample eluted from the column 106, so the fraction collector 310 can collect various sample components based upon their separation. The valve 308 can also direct flow to waste 120. This is useful when the fraction collector 310 is changing collection wells.

As described above, the control system 128 is adapted to control the fraction collector 310. This can be accomplished in a variety of ways, such as by rotating or translating the fraction collector 310 during separation in order to change from one collection vessel to another. In one embodiment, this is based on detection signals from the detector 126. For example, when the elution of the sample component is detected by the detector 126, the valve 308 opens to direct a portion of the effluent flow to the fraction collector 310, and drops the sample component into a collection vessel, such as a test tube, vial or well.

Then, after detection and collection of the component, the valve 308 can be closed momentarily to shut the feed to the fraction collector, at the same time, the fraction collector can be rotated or translated, or the outlet translated to above the next vessel, and the valve 308 is re-opened. The sample components can be dropped successively by repeating this procedure. When the sample components are no longer detected by the detector 126, the valve 308 can be switched to waste 120.

Thus, since only the effluent containing the sample components is fractionated in the vessels and the effluent not containing the sample components is discarded, the vessel is no more used unnecessarily.

Alternatively, in another embodiment, the fraction collector can be controlled to collect fractions "blindly". By this, it is meant that the collector 310 can be controlled to collect a predetermined amount of effluent, either by time or amount, and switching collection vessels every set time period or volume collected.

Figure 4:
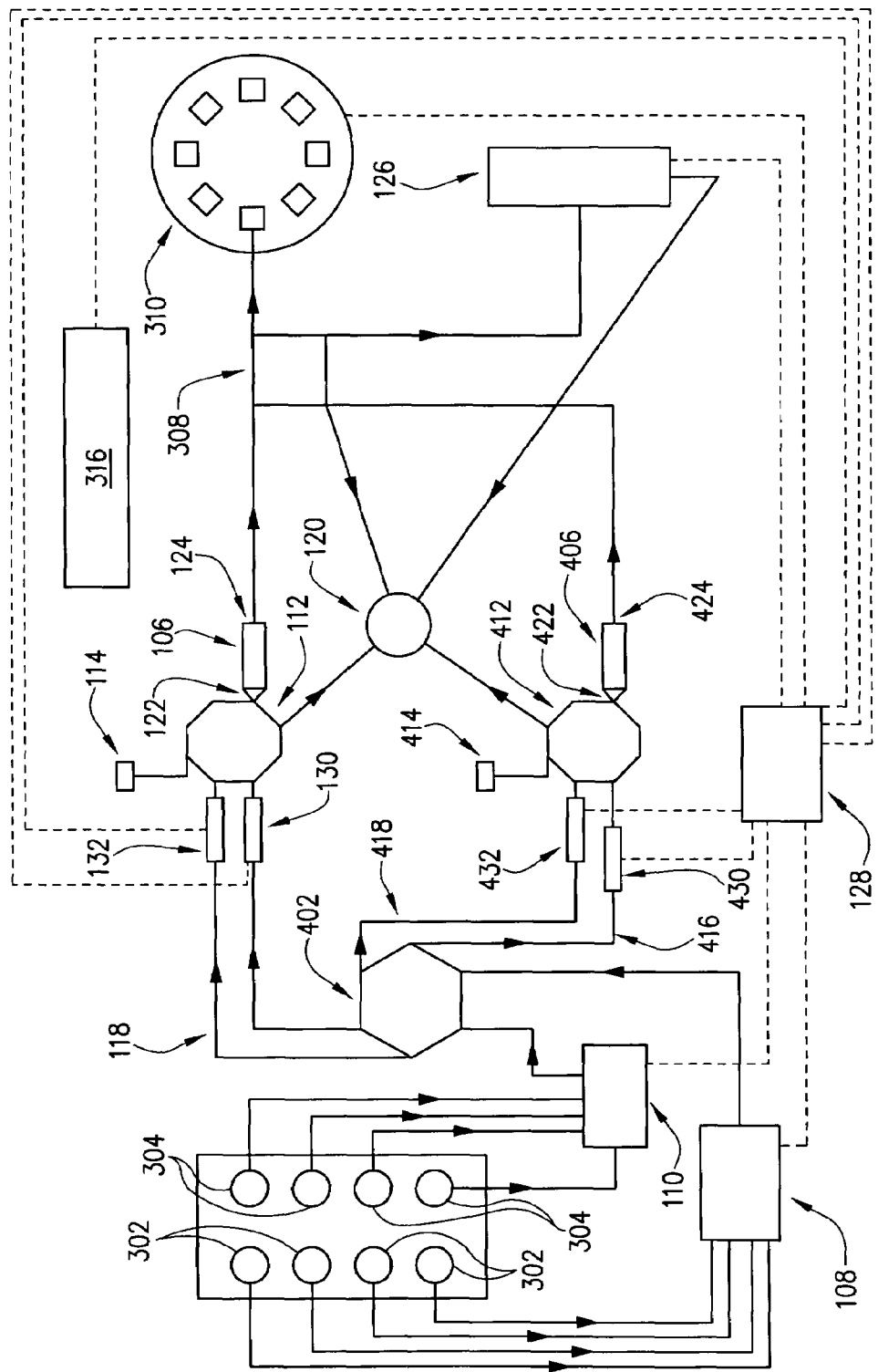
FIG. 4 is a schematic representation of a third embodiment of a liquid chromatography system of the present invention.

FIG. 4 shows another embodiment of a liquid chromatography system of the present invention. In addition to the embodiments shown in FIGS. 1 and 3, the liquid chromatography system 400 additionally includes a second column 406, a second injection port 412 adaptable for fluid communication with the inlet port 422 of the second chromatographic column 406 for injecting samples into the mobile phase, and a valve 402, such as a selection valve, located between and adapted to be in fluid communication with the pumps 108 110 and the first and second injection valves 112 412, and being further adapted to direct the flow of the primary feeds from the pumps 108 110 to the first injection valve 112, the second injection valve 412, or both.

The second injection valve 412 can have the same design as the first injection valve 112, including a primary mixing zone. The second injection valve 412 can be in fluid communication with a waste unit 120 and is fluid communication with the selection valve 402 via a third feed line 416 and a fourth feed line 418. Third 430 and fourth 432 temperature-control elements are in thermal communication with the third and fourth delivery lines 416 418 for maintaining the line temperatures at a predetermined temperature or within a predetermined range of temperatures and heating or cooling the feeds to a predetermined temperature or within a predetermined range of temperatures. The temperature-control elements 430 432 can be, the same as those discussed above. In one embodiment, the third temperature control element 430 is a metal capillary line that is located coaxially inside a tube with re-circulated chilling fluid, and the fourth temperature control element is an electrically heated metal capillary line. In one embodiment, the heated lines 118 418 are maintained at approximately the same temperature, and the chilled lines 116 416 are maintained at approximately the same temperature. In other embodiments, all four lines 116 118 416 418 are all maintained at different temperatures.

In one embodiment the first separation system, which includes the column 106 and injection valve 112 can be designed for an analytical separation (such as a separation for detecting separated components), and the second separation system, which includes the column 406 and the injection valve 412 can be designed for a preparative separation (such as a separation for collecting separated components for further separation or analysis). Analytical separation allows faster separation with smaller sample sizes and gives retention time of peaks as well as shape and profile of the peaks, while preparative separation requires a larger sample size, and has a slower separation time, but involves fraction collection, so in addition to retention time and shapes of the peaks, a further characterization of the separated fractions is possible. In an embodiment such as this, where the system 400 includes an analytical and a preparative system, the injection valve 412 in fluid communication with the preparative column 406, typically has a larger sample loop in order to accommodate larger sample sizes. Also, the preparative column 406 is typically larger than the analytical column 106. In one embodiment, a length of the second chromatographic column 406 is at least one and a half times, and more specifically twice, a length of the first chromatographic column 106. In another embodiment, an inner diameter of the second chromatographic column 406 is at least one and a half times, and more specifically twice, an inner diameter of the first chromatographic column 106. In another embodiment, an internal volume of the second chromatographic column 406 is at least twice, and more specifically three times, an internal volume of the first chromatographic column 106. In another embodiment, the preparative column 406 has a length and diameter approximately twice that of the analytical column 106. In one embodiment, the length of a column used for an analytical separation is preferably between about 2 cm and about 7 cm, and the length of a column used for preparative separation is between about 7 cm and about 12 cm. In another embodiment, the inner diameter of a column used for an analytical separation is preferably between about 2 mm and about 12 mm, and the inner diameter of a column used for preparative separation is between about 15 mm and about 25 mm.

Figure 5:
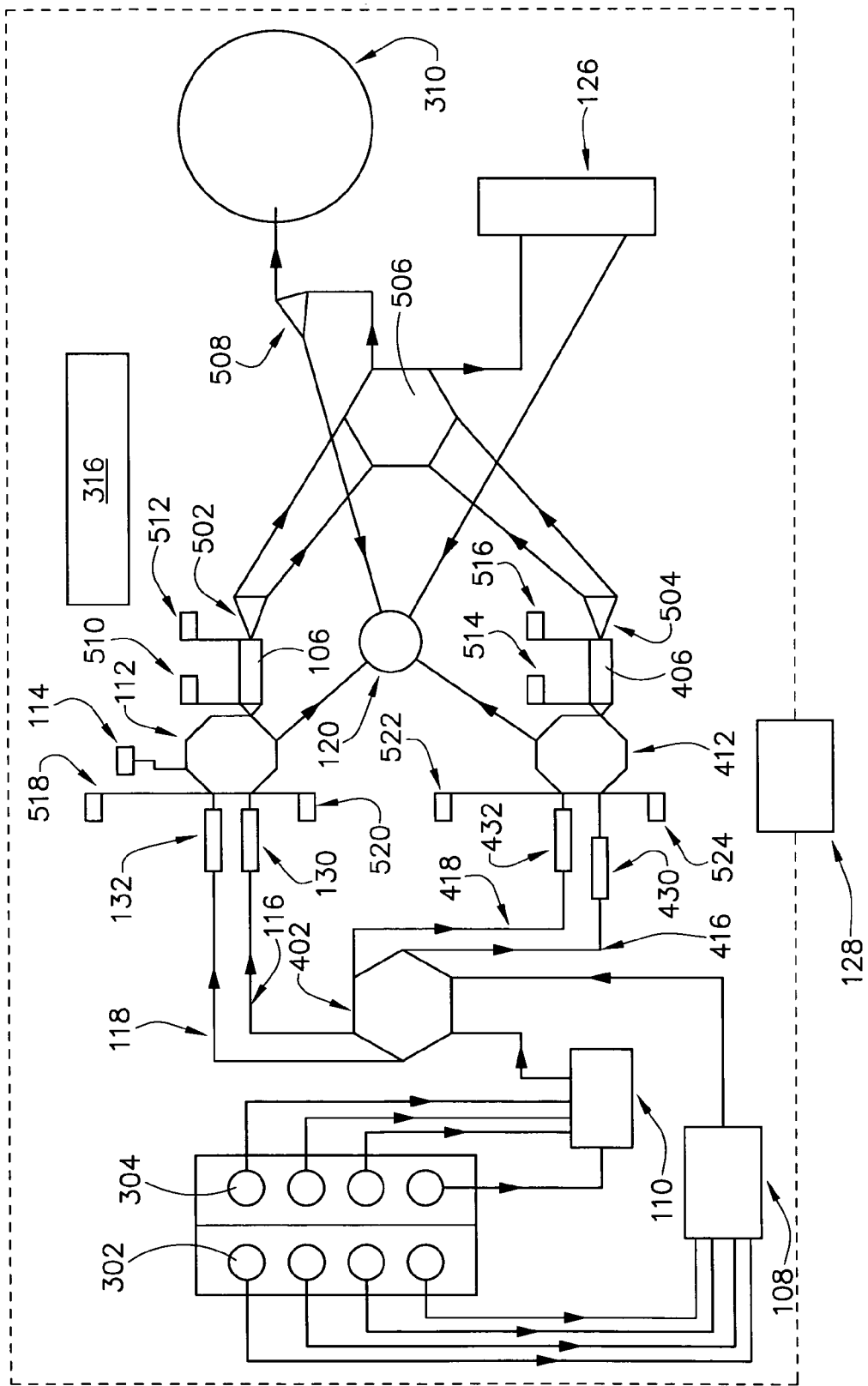
FIG. 5 is a schematic representation of a fourth embodiment of a liquid chromatography system of the present invention.

FIG. 5 shows yet another embodiment of a liquid chromatography system of the present invention. In addition to the embodiments shown in FIG. 4, the liquid chromatography system 500 additionally includes a first splitter valve 502 located at the effluent port of the column 106 and a second splitter valve 504 located at the effluent port of the column 406. The splitters 502 504 act to split the effluent stream and send the streams to a selection valve 506, which directs flow of the effluent to the detector 126 and/or the fraction collector 310. Flow directed to the fraction detector 310 can also pass through a diverter valve 508 which can divert some or all of the flow to a waste collection 120. Also included in this embodiment are thermocouples located at various points of the system 500 in order to monitor temperatures of the various fluids at various points. Thermocouples 510 512 514 516 are located at the inlets and outlets of the columns 106 406 for monitoring the temperatures of the mobile phase directly pre and post column. Thermocouples 518 520 522 524 are located at the inlets of the injection valves 112 412 to monitor the temperatures of the feed streams entering the injectors 112 412.

The combination of splitters 502 504, the selection valve 506, and the diverter valve 508 provide improved detector sensitivity by allowing only the necessary amount to flow through the detector 126. Also, the splitters 502 504 provide the potential for better temperature range and control in the columns 106 406 by allowing higher flow rates. The splitters 502 504 also give each column 106 406 the capability of providing preparative separation. In an embodiment where preparative separation is being carried out, the splitters 502 504 are designed with a high split ratio with most of the flow going to the fraction collector 310. A small amount of sample flows to the detector 126 in order to monitor real time peak changes to aid in the determination of fraction collection.

In operation, with further reference to FIG. 5, for characterization of a single sample, such as a polymer sample, the sample is injected into a mobile phase. The mobile phase and the sample are then delivered through a chromatography column 106, where the sample precipitates and is retained in the column 106. The mobile phase composition and/or temperature is then varied using the control system 128 by varying the flow rates of the various feeds and/or the line temperatures. As the mobile phase is varied by composition and/or temperature and is continuously run through the column 106, various components of the sample are separated in the chromatography column. A property of the separated components of the sample is then detected by the detector 126 and/or collected as fractions in the fraction collector 310.

In one embodiment, the mobile phase is created by mixing a first and second feed, (also known as first and second primary feeds in the presence of secondary feeds) in the injection valve 112 (mixing zone, also known as a primary mixing zone in the presence of secondary mixing zones). In one embodiment, at least a first and a second secondary feed, originating, for example, from a plurality of reservoirs 302, are supplied to a pump 108 (a first secondary mixing zone), where the secondary feeds are mixed into a first primary feed, and at least a third and a fourth secondary feed, originating, for example, from a plurality of reservoirs 304, are supplied to a pump 110 (a second secondary mixing zone), where the secondary feeds are mixed into a second primary feed. The first primary feed from the pump 108 (first secondary mixing zone) is supplied to the injection valve 112 (primary mixing zone) via a first line 116 maintained at a first temperature. The second primary feed is supplied from the pump 110 (second secondary mixing zone) to the injection valve 112 (primary mixing zone) via a second line 118 maintained at a second temperature different than the first temperature.

In another embodiment, at least a first, second, third and fourth secondary feed, originating, for example, from a plurality of reservoirs 302, are supplied to a pump 108 (a first secondary mixing zone), where the four secondary feeds are mixed into a first primary feed, and at least a fifth, sixth, seventh and eighth secondary feed, originating, for example, from a plurality of reservoirs 304, are supplied to a pump 110 (a second secondary mixing zone), where the four secondary feeds are mixed into a second primary feed.

In one embodiment, the lines supplying the first and second feeds 116 118 are maintained at a first and second temperature. One line is heated, while the other line is chilled. The heated line is maintained at a temperature of between about 70° C. and 300° C., more specifically between about 100° C. and 300° C., more specifically between about 150° C. and 300° C., and more specifically between about 220° C. and 280° C. The chilled line is maintained at a temperature of between about −60° C. and 10° C., more specifically between about −30° C. and 0° C., and more specifically between about −20° C. and 0° C.

The unique system described above allows for a variety of operation modes for separation of a material. For example, a separation can be made employing a temperature gradient in combination with a mobile phase composition gradient. By controlling the temperature of the feed lines in the manners described above, in combination with flow rate control of the mobile phase, an achievable separation temperature range from about −15 C. to about 180 C. in the column is possible. The system of the present invention can operate in a variety of separation modes, including, but not limited to: 1) temperature-rising elution fractionation (TREF), which includes running the separation with a strong eluant and raising the temperature from cold to hot, 2) high-temperature, high-performance liquid chromatography (HPLC) system, which includes running the separation at a high temperature and changing the mobile phase composition throughout the separation from a weak eluant to a strong eluant, 3) high-temperature GPC, which includes running a separation at a high temperature with a strong eluant, 4) GPEC (Gradient Polymer Elution Chromatography), 5) low-temperature high-resolution LC, which includes running the separation at room temperature, or colder, while changing the mobile phase composition from a weak eluant to a strong eluant during the separation, 6) room temperature GPC/HPLC, and 7) any combination of those modes, such as a combination of TREF and HPLC by varying both the temperature and the composition of the mobile phase over the course of the separation.

The system of the invention provides versatility in running multiple analysis using the same system by providing the ability to change the separation mode simply by using different temperature and/or solvent systems/gradients within the same system. Also, embodiments employing the two column system, such as those shown in FIGS. 4 and 5, provide the ability for a variety of combinations of separation modes, including, but not limited to: 1) running a two different analytical separations on a sample, 2) running an analytical separation of a sample through a smaller column, and running a preparative separation of the sample through the larger column, 3) running a preparative separation of a sample, then running an analytical separation using different separation conditions on the collected fractions, 4) running a preparative separation of a sample, then running preparative separations using different separation conditions on the collected fractions, then running an analytical separation on the collected fractions using different separation conditions, and 5) running a preparative separation on a sample, and running some other analytical technique on the collected fractions. Some exemplary analytical techniques include: GPC, HPLC, TREF, FTIR, Raman, NMR, AAS, AES, capillary electrophoresis, light scattering, dynamic light scattering, UV-Vis Spectroscopy, birefringence, and fluorescence spectroscopy, other spectroscopic methods known in the art, electrochemistry, such as potentiometry and wet chemistry analysis techniques, such as titrations.

The above described system and modes of operating the system offer a wide variety of applications. For example, the system can provide information regarding crystalline and amorphous distributions in a polymer sample, produce a high throughput crystallinity profiling of a polymer sample can be thoroughly analyzed, provide rapid separation according to chemical composition, such as polar co-monomer incorporation and its distribution, provide information regarding branching distribution, provide separation of polymer blends (using a preparative separation to obtain individual components, and an analytical separation to identify them), provide analysis of polymer extractants, such as small molecule additives, oligomers, and soluble portions, providing higher temperature limits to HPLC and GPC separations, and providing lower temperature limits for separations such as low temperature LC separation of isomers and other closely related compounds, such as small molecules and oligomers. The system also provides the ability for mapping out a multidimensional polymer property distribution space by running multiple separations of the same sample with the separation conditions consistently changing from one mode (such as separating macromolecules primarily according to one property, such as chemical composition) to the other (separating by another property, such as molecular weight), and reconstructing the multidimensional map of properties by composing the multiple separations together. The system also provides for mapping out multidimensional a polymer property distribution space by running a preparative separation of the original sample in one mode and re-running the fractions collected in another separation mode.

Sample-Throughput

For methods directed to characterizing a plurality of samples, a property of each of the samples or of one or more components thereof is detected—serially or in a parallel, serial-parallel or hybrid parallel-serial manner—at an average sample throughput of not more than about 10 minutes per sample. As used in connection herewith, the term "average sample throughput" refers to the sample-number normalized total (cumulative) period of time required to detect a property of two or more polymer samples with a characterization system. The total, cumulative time period is delineated from the initiation of the characterization process for the first sample, to the detection of a property of the last sample or of a component thereof, and includes any intervening between-sample pauses in the process. The sample throughput is more preferably not more than about 8 minutes per sample, even more preferably not more than about 4 minutes per sample and still more preferably not more than about 2 minutes per sample. Depending on the quality resolution of the characterizing information required, the average sample throughput can be not more than about 1 minute per sample, and if desired, not more than about 30 seconds per sample, not more than about 20 seconds per sample or not more than about 10 seconds per sample, and in some applications, not more than about 5 seconds per sample and not more than about 1 second per sample. The average sample-throughput preferably ranges from about 10 minutes per sample to about 10 seconds per sample, more preferably from about 8 minutes per sample to about 10 seconds per sample, even more preferably from about 4 minutes per sample to about 10 seconds per sample and, in some applications, most preferably from about 2 minutes per sample to about 10 seconds per sample.

A sample-throughput of 10 minutes per sample or less is important for a number of reasons. Flow-characterization systems that detect a property of a polymer sample or of a component thereof at the aforementioned sample throughput rates can be employed effectively in a combinatorial polymer research program. From a completely practical point of view, the characterization rates are roughly commensurate with reasonably-scaled polymer sample library synthesis rates. It is generally desirable that combinatorial screening systems, such as the polymer characterization protocols disclosed herein, operate with roughly the same sample throughput as combinatorial synthesis protocols—to prevent a backlog of uncharacterized polymerization product samples. Hence, because moderate scale polymer-synthesis systems, such as the Discovery Tools™ PPR-48™ (Symyx Technologies, Santa Clara Calif.), can readily prepare polymer libraries with a sample-throughput of about 100 polymer samples per day, a screening throughput of about 10 minutes per sample or faster is desirable. Higher throughput synthesis systems demand higher characterization throughputs. The preferred higher throughput values are also important with respect to process control applications, to provide near-real time control data. It is possible, moreover, that a particular sample being characterized may include component that are themselves different analytes of interest, such that the per-analyte throughput for the characterization system can be significantly higher than the per-sample throughput thereof.

Additionally, as shown in connection with the examples provided herein, the characterization of polymer samples at such throughputs can offer sufficiently rigorous quality of data, especially weight-average molecular weight, to be useful for scientifically meaningful exploration of the polymer compositional and/or polymerization reaction conditions research space. Specifically, at sample throughputs ranging from about 10 minutes per sample to about 8 minutes per sample, the polymer sample or one or more components thereof can be characterized with respect to weight-average molecular weight, number-average molecular weight, polydispersity index, molecular weight distribution shape, and conversion information—all at reasonably high quality resolution.

Hence, the average sample-throughput can range, in preferred cases, from about 10 minutes per sample to about 8 minutes per sample, from about 8 minutes per sample to about 2 minutes per sample, from about 2 minutes per sample to about 1 minute per sample, from about 1 minute per sample to about 30 seconds per sample and from about 1 minute per sample to about 10 seconds per sample, with preferences depending on the quality of resolution required in a particular case. For example, in some research strategies, the very high sample throughputs can be effectively employed to efficiently identify a polymer sample or component thereof having a particularly desired property (e.g., such as weight-average molecular weight). In short, the search can be accelerated for the particular property of research interest.

General Features and Protocols

The following features and protocols are general to each of the aforementioned embodiments, and can be applied generally thereto, and used in combination generally therewith.

Generally, the polymer samples being characterized can be non-biological polymers (e.g., non-biological copolymers) or biological polymers (e.g., proteins, DNA), and in many applications, are preferably non-biological polymers. In preferred embodiments, the polymer samples are libraries of polymer samples, such as spatially separated libraries of polymer samples—for example, as a microtiter plate for analysis in an analytical laboratory, or alternatively, such as temporally separated samples such as a series in time of on-line, near real time samples from an polymerization process line—for example, as part of a process monitoring and/or process control system. The libraries of polymer samples can be provided on a common substrate. The libraries of polymer samples can be synthesized in parallel using, for example, a parallel polymerization reactor. The libraries of polymer samples can comprise polymer samples that are polymerization product mixtures resulting from parallel polymerization reactions that are varied with respect to a factor affecting polymerization, such as one or more of reactant materials, catalysts, catalysts precursors, initiators, additives or the relative amounts thereof, or such as polymerization reaction conditions. The libraries of polymer samples can comprise polymer samples that are untreated, or pretreated only with one or more steps selected from the group consisting of non-chromatographic separation, dilution, mixing and redissolution. Further detailed description about the nature of the polymer samples, and/or of libraries of polymer samples, are included in the Co-Owned Rapid Characterization of Polymers Application, a portion of which is reproduced as follows:

Polymer Samples

The present invention is particularly preferred in connection with the characterization of polymer samples, and especially, combinatorial libraries comprising different polymer samples. The polymer sample can be a homogeneous polymer sample or a heterogeneous polymer sample, and in either case, comprises one or more polymer components. As used herein, the term "polymer component" refers to a sample component that includes one or more polymer molecules. The polymer molecules in a particular polymer component have the same repeat unit, and can be structurally identical to each other or structurally different from each other. For example, a polymer component may comprise a number of different molecules, with each molecule having the same repeat unit, but with a number of molecules having different molecular weights from each other (e.g., due to a different degree of polymerization). As another example, a heterogeneous mixture of copolymer molecules may, in some cases, be included within a single polymer component (e.g., a copolymer with a regularly-occurring repeat unit), or may, in other cases, define two or more different polymer components (e.g., a copolymer with irregularly-occurring or randomly-occurring repeat units). Hence, different polymer components include polymer molecules having different repeat units. It is possible that a particular polymer sample (e.g., a member of a library) will not contain a particular polymer molecule or polymer component of interest.

The polymer molecule of the polymer component is preferably a non-biological polymer. A non-biological polymer is, for purposes herein, a polymer other than an amino-acid polymer (e.g., protein) or a nucleic acid polymer (e.g., deoxyribonucleic acid (DNA)). The non-biological polymer molecule of the polymer component is, however, not generally critical; that is, the systems and methods disclosed herein will have broad application with respect to the type (e.g., architecture, composition, synthesis method or mechanism) and/or nature (e.g., physical state, form, attributes) of the non-biological polymer. Hence, the polymer molecule can be, with respect to homopolymer or copolymer architecture, a linear polymer, a branched polymer (e.g., short-chain branched, long-chained branched, hyper-branched), a cross-linked polymer, a cyclic polymer or a dendritic polymer. A copolymer molecule can be a random copolymer molecule, a block copolymer molecule (e.g., di-block, tri-block, multi-block, taper-block), a graft copolymer molecule or a comb copolymer molecule. The particular composition of the non-biological polymer molecule is not critical, and can include repeat units or random occurrences of one or more of the following, without limitation: polyethylene, polypropylene, polystyrene, polyolefin, polyimide, polyisobutylene, polyacrylonitrile, poly(vinyl chloride), poly(methyl methacrylate), poly(vinyl acetate), poly(vinylidene chloride), polytetrafluoroethylene, polyisoprene, polyacrylamide, polyacrylic acid, polyacrylate, poly(ethylene oxide), poly(ethyleneimine), polyamide, polyester, polyurethane, polysiloxane, polyether, polyphosphazine, polymethacrylate, and polyacetals. Polysaccharides are also preferably included within the scope of non-biological polymers. While some polysaccharides are of biological significance, many polysaccharides, and particularly semi-synthetic polysaccharides have substantial industrial utility with little, if any biological significance. Exemplary naturally-occurring polysaccharides include cellulose, dextran, gums (e.g., guar gum, locust bean gum, tamarind xyloglucan, pullulan), and other naturally-occurring biomass. Exemplary semi-synthetic polysaccharides having industrial applications include cellulose diacetate, cellulose triacetate, acylated cellulose, carboxymethyl cellulose and hydroxypropyl cellulose. In any case, such naturally-occurring and semi-synthetic polysaccharides can be modified by reactions such as hydrolysis, esterification, alkylation, or by other reactions.

In typical applications, a polymer sample is a heterogeneous sample comprising one or more polymer components, one or more monomer components and/or a continuous fluid phase. In copolymer applications, the polymer sample can comprise one or more copolymers, a first co-monomer, a second co-monomer, additional co-monomers, and/or a continuous fluid phase. The polymer samples can, in any case, also include other components, such as catalysts, catalyst precursors (e.g., ligands, metal-precursors), solvents, initiators, additives, products of undesired side-reactions (e.g., polymer gel, or undesired homopolymer or copolymers) and/or impurities. Typical additives include, for example, surfactants, control agents, plasticizers, cosolvents and/or accelerators, among others. The various components of the heterogeneous polymer sample can be uniformly or non-uniformly dispersed in the continuous fluid phase.

The polymer sample is preferably a liquid polymer sample, such as a polymer solution, a polymer emulsion, a polymer dispersion or a polymer that is liquid in the pure state (i.e., a neat polymer). A polymer solution comprises one or more polymer components dissolved in a solvent. The polymer solution can be of a form that includes well-dissolved chains and/or dissolved aggregated micelles. The solvent can vary, depending on the application, for example with respect to polarity, volatility, stability, and/or inertness or reactivity. Typical solvents include, for example, tetrahydrofuran (THF), toluene, hexane, ethers, trichlorobenzene, dichlorobenzene, dimethylformamide, water, aqueous buffers, alcohols, etc. According to traditional chemistry conventions, a polymer emulsion can be considered to comprise one or more liquid-phase polymer components emulsified (uniformly or non-uniformly) in a liquid continuous phase, and a polymer dispersion can be considered to comprise solid particles of one or more polymer components dispersed (uniformly or non-uniformly) in a liquid continuous phase. The polymer emulsion and the polymer dispersion can also be considered, however, to have the more typically employed meanings specific to the art of polymer science—of being a emulsion-polymerization product and dispersion-polymerization product, respectively. In such cases, for example, the emulsion polymer sample can more generally include one or more polymer components that are insoluble, but uniformly dispersed, in a continuous phase, with typical emulsions including polymer component particles ranging in diameter from about 2 nm to about 500 nm, more typically from about 20 nm to about 400 nm, and even more typically from about 40 nm to about 200 nm. The dispersion polymer sample can, in such cases, generally include polymer component particles that are dispersed (uniformly or non-uniformly) in a continuous phase, with typical particles having a diameter ranging from about 0.2 µm to about 1000 µm, more typically from about 0.4 µm to about 500 µm, and even more typically from about 0.5 µm to about 200 µm. Exemplary polymers that can be in the form of neat polymer samples include dendrimers, and siloxane, among others. The liquid polymer sample can also be employed in the form of a slurry, a latex, a microgel a physical gel, or in any other form sufficiently tractable for analysis as described and claimed herein. Liquid samples are useful in the automated sample-handling tools that prepare and automatically sample each member of a polymer library. Liquid samples also allow the sample to flow in the chromatographic system or characterization system. In some cases, polymer synthesis reactions (i.e., polymerizations) directly produce liquid samples. These may be bulk liquid polymers, polymer solutions, or heterogeneous liquid samples such as polymer emulsions, lattices, or dispersions. In other cases, the polymer may be synthesized, stored or otherwise available for characterization in a non-liquid physical state, such as a solid state (e.g., crystalline, semicrystalline or amorphous), a glassy state or rubbery state. Hence, the polymer sample may need to be dissolved, dispersed or emulsified to form a liquid sample by addition of a continuous liquid-phase such as a solvent. The polymer sample can, regardless of its particular form, have various attributes, including variations with respect to polarity, solubility and/or miscibility.

In preferred applications, the polymer sample is a polymerization product mixture. As used herein, the term "polymerization product mixture" refers to a mixture of sample components obtained as a product from a polymerization reaction. An exemplary polymerization product mixture can be a sample from a combinatorial library prepared by polymerization reactions, or can be a polymer sample drawn off of an industrial process line. In general, the polymer sample may be obtained after the synthesis reaction is stopped or completed or during the course of the polymerization reaction. Alternatively, samples of each polymerization reaction can be taken and placed into an intermediate array of vessels at various times during the course of the synthesis, optionally with addition of more solvent or other reagents to arrest the synthesis reaction or prepare the samples for analysis. These intermediate arrays can then be characterized at any time without interrupting the synthesis reaction. It is also possible to use polymer samples or libraries of polymer samples that were prepared previously and stored. Typically, polymer libraries can be stored with agents to ensure polymer integrity. Such storage agents include, for example, antioxidants or other agents effective for preventing cross-linking of polymer molecules during storage. Depending upon the polymerization reaction, other processing steps may also be desired, all of which are preferably automated. The polymerization scheme and/or mechanism by which the polymer molecules of the polymer component of the sample are prepared is not critical, and can include, for example, reactions considered to be addition polymerization, condensation polymerization, step-growth polymerization, and/or chain-growth polymerization reactions. Viewed from another aspect, the polymerization reaction can be an emulsion polymerization or a dispersion polymerization reaction. Viewed more specifically with respect to the mechanism, the polymerization reaction can be radical polymerization, ionic polymerization (e.g., cationic polymerization, anionic polymerization), and/or ring-opening polymerization reactions, among others. Non-limiting examples of the foregoing include, Ziegler-Natta or Kaminsky-Sinn reactions and various copolymerization reactions. Polymerization product mixtures can also be prepared by modification of a polymeric starting materials, by grafting reactions, chain extension, chain scission, functional group interconversion, or other reactions.

The sample size is not narrowly critical, and can generally vary, depending on the particular characterization protocols and systems used to characterize the sample or components thereof. Typical sample sizes can range from about 0.1 µl to about 1 ml, more typically from about 1 µl to about 1000 µl, even more typically from about 5 µl to about 100 µl, and still more typically from about 10 µl to about 50 µl. A generally preferred sample size for flow characterization systems and, particularly for liquid chromatography, is a sample size of about 20 µl.

The polymer sample, such as a polymerization product mixture, can be a raw, untreated polymer sample or can be pretreated in preparation for characterization. Typical sample preparation steps include preliminary, non-chromatographic separation of one or more components of a polymer sample from other components, dilution, mixing and/or redissolution (e.g., from a solid state), among other operations. Preliminary separation methods can help remove large-scale impurities such as dust, coagulum or other impurities. Such separation methods can include, for example: filtering (e.g., with a microfilter having pore sizes that allow the passage of particles less than about 0.5 µm or 0.2 µm); precipitation of polymer components, monomer components and/or other small-molecule components, decanting, washing, scavenging (e.g., with drying agents), membrane separation (e.g., diafiltration, dialysis), evaporation of volatile components and/or ion-exchange. The sample is preferably diluted, if necessary, to a concentration range suitable for detection. For typical liquid chromatography applications, for example, the sample concentration prior to loading into the liquid chromatography system can range from about 0.01 mg/ml to a neat sample, more typically from about 0.01 mg/ml to about 100 mg/ml, and even more typically from about 0.1 mg/ml to about 50 mg/ml. More specific concentration ranges typical for liquid chromatography samples include from about 0.1 mg/ml to about 20 mg/ml, and from about 0.5 mg/ml to about 5 mg/ml. For flow-injection analysis systems, in which the sample is detected without substantial chromatographic separation thereof, much more dilute solutions can be employed. Hence, the concentration can range from a detectable concentration level (for the particular detector employed) up to about 1 mg/ml, or more in some applications. Typical concentrations can be about $1 \times 10^{-2}$ wt %, about $1 \times 10^{-3}$ wt % or about $1 \times 10^{-4}$ wt %. Mixing can be required to increase the uniformity of a polymer sample emulsion or dispersion, and/or to integrate one or more additional components into the polymer sample. Preparation steps, and particularly rapid preparation techniques, can be an important aspect for combinatorial polymer investigations—since polymer samples may be synthesized in a form not ideally suited for immediate characterization.

Although the primary applications of the present invention are directed to combinatorial polymer science research and/or quality control for industrial polymer synthesis or processing protocols, aspects of the invention can have applications involving non-polymer samples. A non-polymer sample can be a material that comprises an organic or an inorganic non-polymer element or compound. Oligomers are considered to be polymers rather than non-polymers. The non-polymer molecule is, in some cases, preferably a non-biological non-polymer element or compound. Such non-biological non-polymer elements or compounds include non-polymer elements or compounds other than those having a well-characterized biological activity and/or a primary commercial application for a biological field (e.g., steroids, hormones, etc.). More particularly, such non-biological, non-polymer elements or compounds can include organic or inorganic materials such as pigments, carbon powders (e.g., carbon black), metals, metal oxides, metal salts, metal colloids, metal ligands, etc, without particular limitation.

Pluralities of Samples/Libraries of Samples

A plurality of samples such as polymer samples comprises 2 or more samples that are physically or temporally separated from each other—for example, by residing in different sample containers, by having a membrane or other partitioning material positioned between samples, by being partitioned (e.g., in-line) with an intervening fluid, by being temporally separated in a flow process line (e.g., as sampled for process control purposes), or otherwise. The plurality of samples preferably comprises 4 or more samples, more preferably 8 or more samples, and even more preferably 10 or more samples. Four samples can be employed, for example, in connection with experiments having one control sample and three polymer samples varying (e.g., with respect to composition or process conditions as discussed above) to be representative of a high, a medium and a low-value of the varied factor—and thereby, to provide some indication as to trends. Eight samples can provide for additional variations in the explored factor space. Moreover, eight samples corresponds to the number of parallel polymerization reactors in the PPR-8™, being selectively offered as one of the Discovery Tools™ of Symyx Technologies, Inc. (Santa Clara, Calif.). Higher numbers of samples can be investigated, according to the methods of the invention, to provide additional insights into larger compositional and/or process space. In some cases, for example, the plurality of samples can be 15 or more samples, preferably 20 or more samples, more preferably 40 or more samples and even more preferably 80 or more samples. Such numbers can be loosely associated with standard configurations of parallel reactor configurations (e.g., the PPR-48™, Symyx Technologies, Inc.) and/or of standard sample containers (e.g., 96-well microtiter plate-type formats). Moreover, even larger numbers of samples such as polymer samples can be characterized according to the methods of the present invention for larger scale research endeavors. Hence, the number of samples can be 150 or more, 400 or more, 500 or more, 750 or more, 1,000 or more, 1,500 or more, 2,000 or more, 5,000 or more and 10,000 or more polymer samples. As such, the number of samples can range from about 2 samples to about 10,000 samples, and preferably from about 8 samples to about 10,000 samples. In many applications, however, the number of samples can range from about 80 samples to about 1500 samples. In some cases, in which processing of samples using typical 96-well microtiter-plate formatting is convenient or otherwise desirable, the number of samples can be 96*N, where N is an integer ranging from about 1 to about 100. For many applications, N can suitably range from 1 to about 20, and in some cases, from 1 to about 5.

The plurality of samples can be a combinatorial library of samples. A library of samples comprises of two or more different samples, and can be in an array format as spatially separated samples—preferably on a common substrate, or temporally separated—for example, in a flow system. Candidate samples (i.e., members) within a library may differ in a definable and typically predefined way, including with regard to chemical structure, processing (e.g., synthesis) history, mixtures of interacting components, purity, etc. The samples can be spatially separated, preferably at an exposed surface of the substrate, such that the array of samples are separately addressable for sampling into the characterization system and subsequent characterization thereof. The two or more different samples can reside in sample containers formed as wells in a surface of the substrate. The number of samples included within the library can generally be the same as the number of samples included within the plurality of samples, as discussed above. In general, however, not all of the samples within a library of samples need to be different samples. When process conditions are to be evaluated, the libraries may contain only one type of sample. Typically, however, for combinatorial polymer science research applications, at least two or more, preferably at least four or more, even more preferably eight or more and, in many cases most, and allowably each of the plurality of polymer samples in a given library of polymer samples will be different from each other. Specifically, a different polymer sample can be included within at least about 50%, preferably at least 75%, preferably at least 80%, even more preferably at least 90%, still more preferably at least 95%, yet more preferably at least 98% and most preferably at least 99% of the polymer samples included in the sample library. In some cases, all of the polymer samples in a library of polymer samples will be different from each other.

The substrate can be a structure having a rigid or semi-rigid surface on which or into which the array of polymer samples can be formed or deposited. The substrate can be of any suitable material, and preferably consists essentially of materials that are inert with respect to the polymer samples of interest. Certain materials will, therefore, be less desirably employed as a substrate material for certain polymerization reaction process conditions (e.g., high temperatures—especially temperatures greater than about 100° C.—or high pressures) and/or for certain reaction mechanisms. Stainless steel, silicon, including polycrystalline silicon, single-crystal silicon, sputtered silicon, and silica ($SiO_2$) in any of its forms (quartz, glass, etc.) are preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. Organic and inorganic polymers may also be suitably employed in some applications of the invention. Exemplary polymeric materials that can be suitable as a substrate material in particular applications include polyimides such as Kapton™, polypropylene, polytetrafluoroethylene (PTFE) and/or polyether etherketone (PEEK), among others. The substrate material is also preferably selected for suitability in connection with known fabrication techniques. As to form, the sample containers formed in, at or on a substrate can be preferably, but are not necessarily, arranged in a substantially flat, substantially planar surface of the substrate. The sample containers can be formed in a surface of the substrate as dimples, wells, raised regions, trenches, or the like. Non-conventional substrate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications. In preferred embodiments, the substrate is designed such that the individually addressable regions of the substrate can act as polymerization reaction vessels for preparing a polymerization product mixture (as well as sample containers for the two or more different polymer samples during subsequent characterization thereof. Glass-lined, 96-well, 384-well and 1536-well microtiter-type plates, fabricated from stainless steel and/or aluminum, are preferred substrates for a library of polymer samples. The choice of an appropriate specific substrate material and/or form for certain applications will be apparent to those of skill in the art in view of the guidance provided herein.

The library of polymer materials can be a combinatorial library of reaction product mixtures such as polymerization product mixtures. Polymer libraries can comprise, for example, polymerization product mixtures resulting from polymerization reactions that are varied with respect to, for example, reactant materials (e.g., monomers, co-monomers), catalysts, catalyst precursors, initiators, additives, the relative amounts of such components, reaction conditions (e.g., temperature, pressure, reaction time) or any other factor affecting polymerization. Design variables for polymerization reactions are well known in the art. See generally, Odian, *Principles of Polymerization*, $3^{rd}$ Ed., John Wiley & Sons, Inc. (1991). A library of polymer samples may be prepared in arrays, in parallel polymerization reactors or in a serial fashion. Exemplary methods and apparatus for preparing polymer libraries—based on combinatorial polymer synthesis approaches—are disclosed in copending U.S. patent application Ser. No. 09/211,982 of Turner et al. filed Dec. 14, 1998, copending U.S. patent application Ser. No. 09/227,558 of Turner et al. filed Jan. 8, 1999, copending U.S. patent application Ser. No. 09/235,368 of Weinberg et al. filed Jan. 21, 1999, and copending U.S. provisional patent application Ser. No. 60/122,704 entitled "Controlled, Stable Free Radical Emulsion and Water-Based Polymerizations", filed Mar. 9, 1999 by Klaerner et al. See also, PCT Patent Application WO 96/11878.

The libraries can be advantageously characterized directly, without being isolated, from the reaction vessel in which the polymer was synthesized. Thus, reagents, catalysts or initiators and other additives for making polymers may be included with the polymer sample for characterization or screening.

While such methods are preferred for a combinatorial approach to polymer science research, they are to be considered exemplary and non-limiting. As noted above, the particular polymer samples characterized according to the methods and with the apparatus disclosed herein can be from any source, including, but not limited to polymerization product mixtures resulting from combinatorial synthesis approaches.

Non-Polymer Samples

Although the primary applications of the present invention are directed to combinatorial polymer science research and/or quality control for industrial polymer synthesis or processing protocols, some aspects of the invention can have applications involving non-polymer samples. A non-polymer sample can be a material that comprises an organic or an inorganic non-polymer element or compound. Oligomers are considered to be polymers rather than non-polymers. The non-polymer molecule is, in some cases, preferably a non-biological non-polymer element or compound. Such non-biological non-polymer elements or compounds include non-polymer elements or compounds other than those having a well-characterized biological activity and/or a primary commercial application for a biological field (e.g., steroids, hormones, etc.). More particularly, such non-biological, non-polymer elements or compounds can include organic or inorganic pigments, carbon powders (e.g., carbon black), metals, metal oxides, metal salts, metal colloids, metal ligands, etc, without particular limitation.

Detectors/Detected Properties/Determined Properties

A polymer sample is characterized by detecting a property of the polymer sample, or by detecting a property of a component (e.g., a polymer component, a monomer component) of the polymer sample. In many cases, the property is detected over a period of time, such that a variation in the property can be observed or detected or the rate of change of variation of a property can be observed or detected. In the general case, the detected property can be any property, which can provide a scientifically meaningful basis of comparison between two different polymer samples or between two different polymer components—either directly, or after being correlated to a specific characterizing property of interest. The detected property can be a chemical property or a physical property of the polymer sample or component thereof. In preferred applications, an optical property of the polymer sample or a component thereof can be detected. For example, an amount, frequency, intensity or direction of an incident light that is refracted, scattered, and/or absorbed by the polymer sample or a component thereof may be detected. Other properties, such as pressure or other factors affecting a particular characterizing property of interest (e.g., viscosity) can likewise be detected.

As described above, a property of a polymer sample or of a component thereof, such as a chromatographically separated component thereof, can be detected in a flow characterization system with one or more detectors. In some embodiments, a property of a polymer sample or of a component thereof is detected with an optical detector such as a refractive-index detector, an ultraviolet-visual detector, a photodiode array detector, a static-light-scattering detector, a dynamic-light-scattering detector, and/or an evaporative-light-scattering detector—also known as an evaporative mass detector EMD). Other detectors (e.g., a capillary viscometer detector, photodiode array detector PDAD), infra-red detector, fluorescence detector, electrochemical detector, conductivity detector, etc.) can likewise be employed in connection with the present invention. The particular nature of the detector (e.g., shape and/or configuration of a detection cavity 131 within the detector) is not generally critical.

The protocols for characterizing one or more polymer samples preferably further comprise determining a property of interest from the detected property. The physically-detected properties, such as the capability of the polymer sample or component thereof to refract, scatter, emit or absorb light can be correlated to properties of interest. Such properties of interest include, without limitation, weight-average molecular weight, number-average molecular weight, viscosity-average molecular weight, peak molecular weight, approximate molecular weight, polydispersity index, molecular-weight-distribution shape, relative or absolute component concentration, chemical composition, conversion, concentration, mass, hydrodynamic radius ($R_h$), radius of gyration ($R_g$), chemical composition, amounts of residual monomer, presence and amounts of other low-molecular weight impurities in polymer samples, particle or molecular size, intrinsic viscosity, molecular shape, molecular conformation, and/or agglomeration or assemblage of molecules. The correlation between a detected property and a determined property of interest can be based on mathematical models and/or empirical calibrations. Such correlation methods are generally known in the art, and are typically incorporated into commercially-available chromatographic detectors and/or detector or data-acquisition software.

For combinatorial polymer science research applications, as well as other applications, the characterization protocols can be effected to determine at least a weight-average molecular weight as a characterization property of primary importance. Other characterization properties of interest of substantial importance, include number-average molecular weight, polydispersity index, and molecular-weight-distribution shape. For polymer samples that are polymerization product mixtures, another characterization property of substantial importance is conversion data for the polymerization reaction, typically expressed as % monomer converted into polymer. The composition of the polymer sample or of particular components thereof (e.g., polymer components) can also be of substantial importance.

For determining weight-average molecular weight from detected properties, a liquid chromatography system can advantageously employ a single detector or a combination of two or more detectors. In a single-detector embodiment, for example, a dynamic light-scattering (DLS) detector can be used by itself to determine an average hydrodynamic radius or a distribution of hydrodynamic radii from the detected scattered light. The hydrodynamic radii can, in turn, be correlated to an average molecular weight or a molecular weight distribution. In a two-detector embodiment, for example, a static-light scattering (SLS) detector (where the detected scattered light is a function of weight-average molecular weight ($M_w$), concentration (C) and the square of the refractive index increment, $(dn/dC)^2$) can be combined with a refractive index (RI) detector (where the detected refracted light is a function of (C) and (dn/dC)), with an ultraviolet/visible light absorbance (UV/VIS) detector (where the detected absorbed light is a function of (C)), or with an evaporative light scattering detector (ELSD) (where the detected scattered light is a function of (C)). In another embodiment, a single-detector or multiple detectors (e.g., SLS) can detect the intensity of light scattered by the sample or sample component at two or more different angles, which can be correlated to molecular weight.

For polymer samples that are polymerization product mixtures, conversion data for the polymerization reaction of which the sample is representative can be determined by chromatographically resolving the polymer component(s) and monomer component(s), determining a molecular-weight distribution for such components, integrating areas under the respective peaks, and then comparing the integrated peak areas (e.g., using response factors for particular components and detector employed). Another approach for calculating conversion involves converting the polymer-peak area into polymer concentration or mass using a concentration-detector response calibration plot, and then comparing the portion of the polymer mass or concentration found in the sample to the expected mass or concentration assuming 100% stoichiometric conversion. Composition data for a polymer sample can be determined from the consumption of monomer or comonomers or, alternatively, from a retention time per volume of the polymer peak or a fraction thereof.

Advantageously, an ELSD detector, or other detectors that are not particularly sensitive to low-molecular weight components of a polymer sample, can be advantageously employed in connection with the flow characterization protocols of the invention to achieve a high sample-throughput.

As discussed in greater detail below, detectors that are insensitive to low-molecular weight components can be advantageously employed in connection with rapid-serial overlapping techniques. Moreover, because the ELSD is also less sensitive to temperature variations than other types of mass detectors (e.g., RI detector) and is not required to be in thermal equilibrium with the sample being detected, an ELSD detector can be employed advantageously in connection with high-temperature polymer characterization systems. Hence, detecting a property of a polymer sample or a component there of with an ELSD or with other low-MW insensitive or less temperature sensitive mass detectors provides a further aspect for improving the sample throughput—particularly for a liquid chromatography system.

The aforementioned characterizing properties of interest can, once determined, be mathematically combined in various combinations to provide figures of merit for various properties or attributes of interest. In particular, for example, molecular weight, conversion and polydispersity index can be evaluated versus polymerization process time to provide mechanistic insights as to how polymers are formed. Other combinations of the fundamental characterization properties of interest will be apparent to those of skill in the art.

Automated Preparation/Sampling

A plurality of polymer samples, such as those included within a library of polymer samples, is preferably delivered to the injection valve 112, for loading into the flow characterization system, with an automatic delivery device, such as an auto-sampler. As used herein, the term "auto-sampler" refers to an apparatus suitable for automated sampling of polymer samples for characterization, including automated withdrawal of a polymer sample from a sample container, and automated loading of at least a portion of the withdrawn sample into an injection port or a loading port of a flow characterization system (e.g. a liquid chromatography system).

Automated sampling equipment is available commercially for introducing multiple samples into liquid flow systems in a serial manner. While such commercially-available auto-sampling equipment could be used with this invention, currently available systems have several drawbacks. First, commercially available auto-samplers typically operate with a single predefined rack or tray configuration, which contains vials in a rectangular, linear, or rotary array. Samples are loaded manually and individually into vials, and manually placed in the array for subsequent sampling. The combinatorial aspects of this invention, however, prefer automated sample preparation of vast numbers of samples, from a variety of parallel vessel arrays or reactor blocks. Additionally, commercial auto-sampling equipment is not sufficiently rapid. Conventional auto-samplers require up to several minutes per cycle to introduce a polymer sample into a flow characterization system—including steps such as sample changing, drawing, loading, and cleaning of the system in preparation for the next sample. For the purposes of this invention, more rapid sample introduction is desirable—preferably requiring much less than one minute per sample. Moreover, conventional commercially-available auto-sampling equipment is not designed for complex sample preparation, including transfer, dilution, purification, precipitation, or other steps needed to prepare elements of a combinatorial array for characterization.

As such, aspects of this invention include an auto-sampler and auto-sampling methods, such as those described in U.S. Pat. No. 6,492,184 to Petro et al, the disclosure of which is hereby incorporated by reference.

Specific applications and/or combinations of detectors, as well as correlation protocols, are discussed in greater detail below

EXAMPLES

FIGS. 6A through 6D are graphical data showing the attainable temperature controls for the environments in the columns of the liquid chromatography system of the present invention by controlling line temperatures, flow rates of solvents and compositional control of solvent mixtures.

FIG. 6A is a plot showing the temperature of the mobile phase at the inlet of the column after fifteen minutes. The plot shows temperature monitored at the inlet of the column versus the temperature of the heated line for various flow rates. Flow rates of 3, 4 and 5 mL/minute of fluid where run through the system, with the hot line temperature ranging from 200° C. to 300° C. Data points were collected when the temperature of the electrically heated line reached 200, 220, 240, 260, 280 and 300° C. For the various flow rates, temperatures of the fluids at the inlet of the column ranging from about 130° C. to about 220° C. were accomplished.

FIG. 6B is a plot showing the temperature of the mobile phase at the outlet of the column after fifteen minutes. The column was 4 cm in length. The hotline temperatures ranged from 200 to 300° C. and the fluids were run at flow rates of 3, 4 and 5 mL/minute. The plot shows temperature monitored at the outlet of the column versus the temperature of the heated line for various flow rates. For the various flow rates, temperatures of the fluids at the outlet of the column ranging from about 100° C. to about 190° C. were accomplished.

FIG. 6C is a plot showing the temperature of the mobile phase at the outlet of the column after twenty minutes while varying the heated and chilled feeds. The plot shows temperature monitored at the outlet of the column versus the percentage of heated mobile phase fluid in the mobile phase for various flow rates with the heated line set at 280° C. and the chilled line set at −16° C. Fluids were run through the system at flow rates of 2,3,4 and 5 mL/minute, and the percentage of feed from the heated line varied from 0% to 100%. For the various flow rates, temperatures of the fluids at the outlet of the column ranging from about 20° C. to about 180° C. were accomplished.

FIG. 6D is a plot showing the monitored temperature versus the mobile phase flow rate for various compositions at both the inlet and the outlet of a 4 cm length column, for 100% hot line flow and a 100% chilled line flow. The heated line was set at 280° C. and the chilled line was set at −16° C. Fluids were run through the system at flow rates of 1, 2, 3 and 4 mL/minute. For the various flow rates, temperatures of the fluids in column for the heated feed ranged from about 120° C. to about 200° C., and temperatures of the fluids in column for the chilled feed ranged from about 25° C. to about 0° C.

Polymer Separations

The following examples demonstrate the use of a chromatography system as shown and described in FIG. 5 for chromatographic separation of polymers using TREF chromatography with a temperature gradient during separation and a combination of HPLC and TREF, chromatography with a temperature and a mobile phase gradient during separation. The examples utilize the analytical portion of the system, running sample through an analytical column.

In the following examples, three samples as described below in Table 1 were used:

TABLE 1

| Sample ID | Source | Product | Product Description | Density | $I_2$ | Tm (DSC) | mol % Hexene by NMR | mol % Hexene by FTIR | Mw(k) | PDI |
|---|---|---|---|---|---|---|---|---|---|---|
| X | Chevron Phillips Chemical Company | mPact D449 | Metallocene LLDPE | 0.945 | 0.8 | 130 | 0.5 | 1 | 236 | 1.9 |
| Y | ExxonMobil Chemical Company | Exceed 1012CA | Metallocene LLDPE | 0.912 | 1.0 | 115 | 4.0 | 4 | 194 | 1.7 |
| Z | ExxonMobil Chemical Company | Exact 4056 | Ethylene-hexene copolymer Plastomer | 0.883 | 2.2 | 72 | 10.1 | 10 | 169 | 1.6 |

The injection valve as shown in FIG. 2 was fitted with one sample loop (having a 50 microliter volume) in combination with a chromatographic apparatus comprising a two-pump gradient chromatography system. A 5 cm length×1 cm inner diameter column made of High-Temp PEEK material was utilized. The column was packed with 5 micron macroporous silica gel packing available from Nucleosil in Macherey-Nagel, Germany. The column was proximately coupled to the injection valve as shown in FIG. 1A. The system was configured such that the combined flow of a heated line set to 260° C. and a chilled line set to −10° C. passed through the valve, the column, and then to an ELSD chromatographic detector. The entire system, including pump control and data acquisition from the detector was computer-controlled.

The three commercially available polymers were dissolved in trichlorobenzene at a nominal concentration of 2 mg/mL. 200 μL of each of these polymer samples were serially injected into the mobile phase of the liquid chromatography system while varying a range of chromatographic parameters, including temperature gradient and gradient composition, to obtain reasonable separation of the various samples in a short time.

TREF Separation

In one set of experiments, separation utilized a temperature gradient of one solvent. One reservoir of dichlorobenzene was used for the hot line and one reservoir of dichlorobenzene was utilized for the chilled line. The following conditions were chosen:

TABLE 2

Mobile-Phase Conditions

| Time (min) | Parameter | Value |
|---|---|---|
| 0.0 | Total flow | 3 mL/min. |
| 0.0 | Starting Solvent Composition | 100% dichlorobenzene, both hot and cold lines 99:1 cold/hot line flow ratio |
| 3.00 | Begin Linear Gradient | From 99:1 to 1:99 cold/hot line flow ratio |
| 6.00 | End Gradient | maintain 1:99 cold/hot line flow ratio |
| 16.00 | Begin Linear Gradient | return back to 99:1 cold/hot ratio in 1 min |
| 17.00 | Initial Solvent Composition | Reestablished 99:1 cold/hot line flow ratio |

Using the chromatographic conditions described above, the following peak retention times for the standards were measured:

TABLE 3

Peak Retention Times for Samples

| Sample | Peak Center | $T_m$ (DSC) |
|---|---|---|
| X | 870 | 130 |
| Y | 519 | 115 |
| Z | 403 | 72 |

Figure 7A:
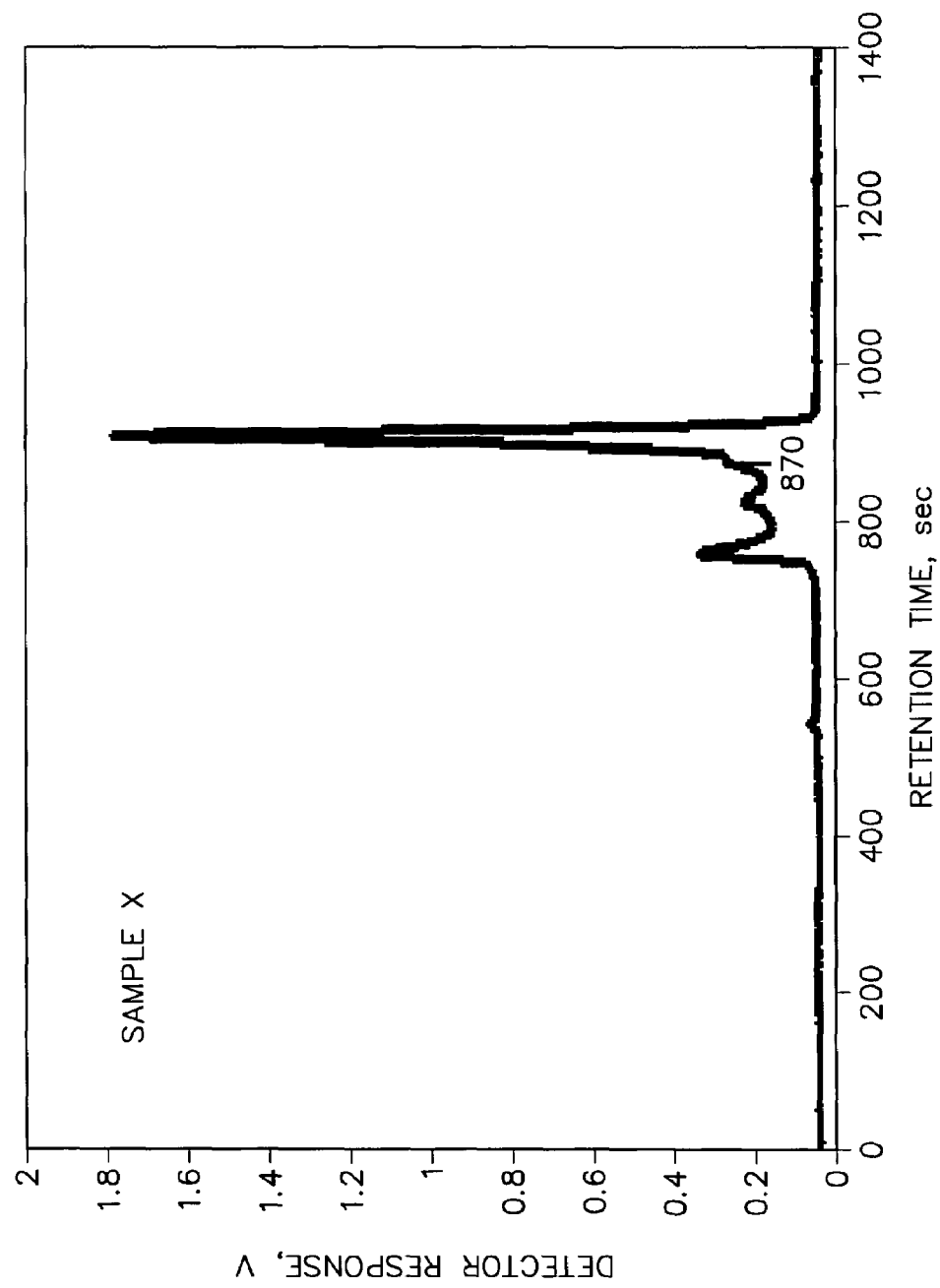
FIG. 7A is a chromatogram of the TREF analysis of Sample X as described in the Examples.
Figure 7B:
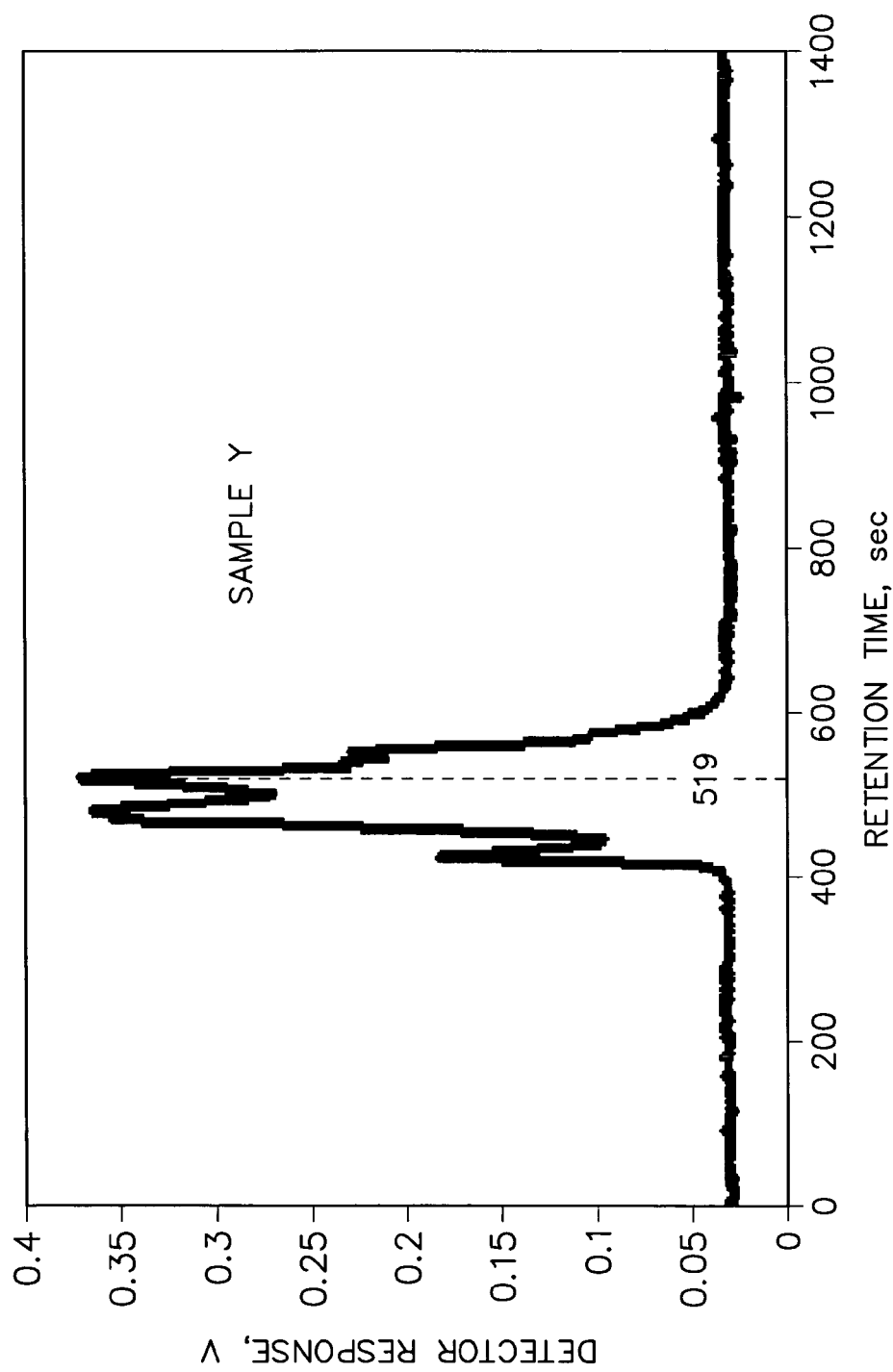
FIG. 7B is a chromatogram of the TREF analysis of Sample Y as described in the Examples.
Figure 7C:
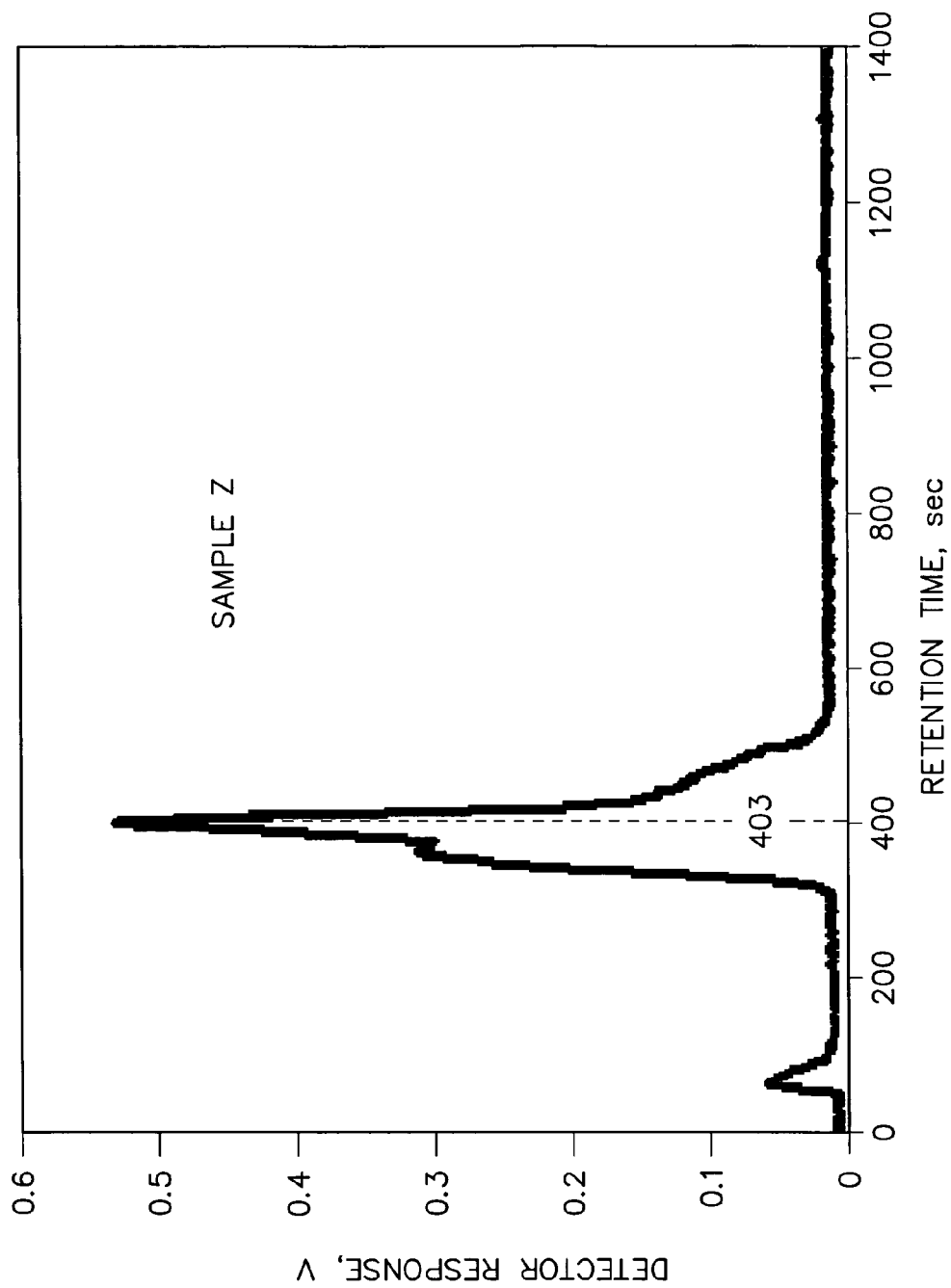
FIG. 7C is a chromatogram of the TREF analysis of Sample Z as described in the Examples.
Figure 7D:
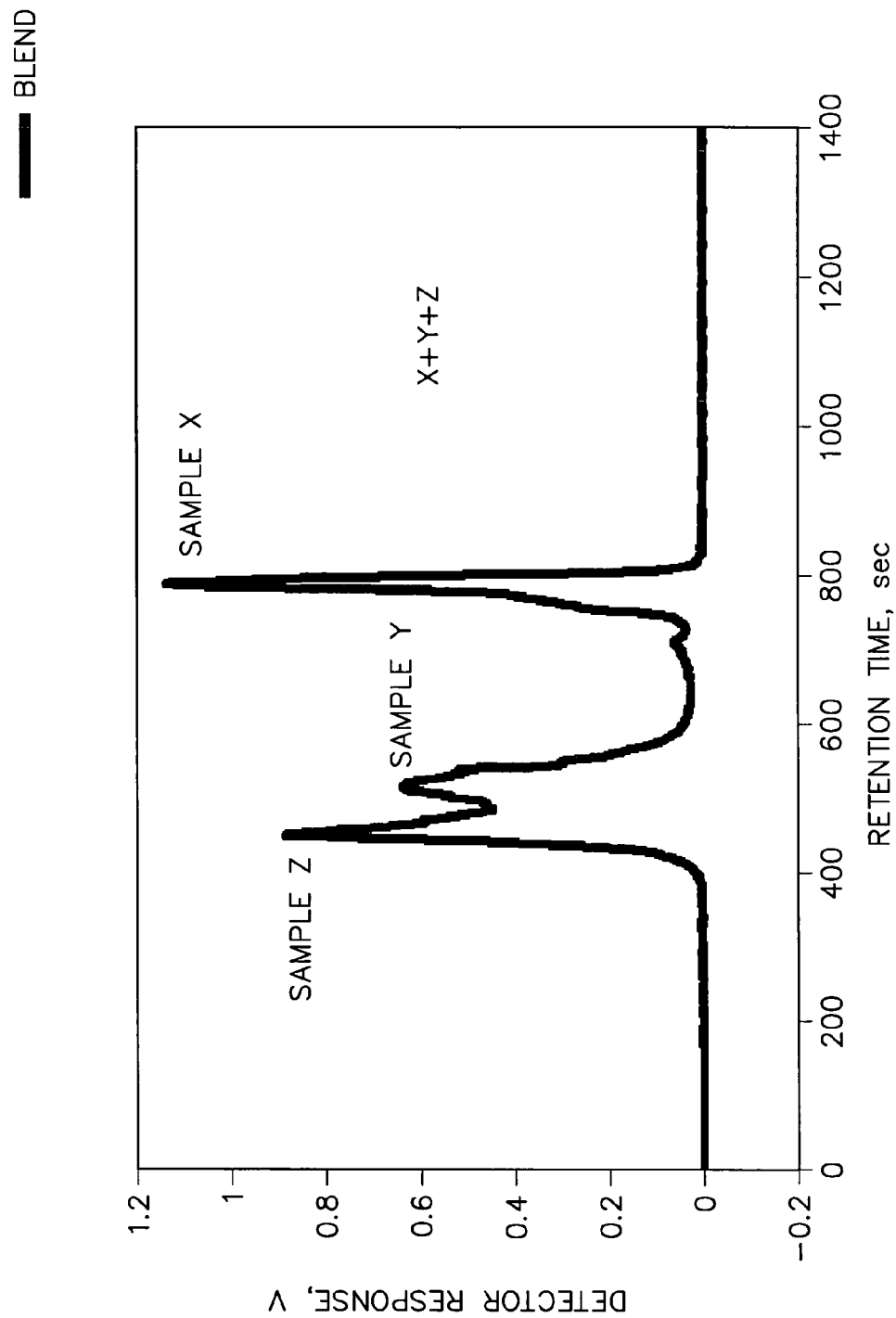
FIG. 7D is a chromatogram of the TREF separation analysis of the blend of Samples X, Y and Z as described in the Examples.

The chromatograms for the three separated samples as described above are shown in FIG. 7A for sample X, FIG. 7B for sample Y and FIG. 7C for sample Z. The three samples were then blended in a 1:1:1 ratio and separated under similar conditions. The chromatogram of the separated blend is shown in FIG. 7D.

Separations Combining TREF and HPLC

In another experiment, separation utilized a temperature gradient and a solvent gradient. One reservoir of dichlorobenzene and one reservoir of isopropyl alcohol were used to feed the chilled line in a volume ratio of 97% dichlorobenzene and 3% isopropyl alcohol. One reservoir of dichlorobenzene and one reservoir of tetrahydrofuran were used to feed the heated line in a volume ratio of 97% dichlorobenzene and 3% tetrahydrofuran. The three samples were blended in a 1:1:1 ratio and separated under the following conditions shown in Table 4:

TABLE 4

Mobile-Phase Conditions

| Time (min) | Parameter | Value |
|---|---|---|
| 0.0 | Total flow | 3 mL/min. |
| 0.0 | Starting Solvent Composition | 3% isopropyl alcohol and 97% dichlorobenzene in cold line (vol./vol.) 3% tetrahydrofuran and 97% dichlorobenzene in hot line (vol./vol.) 99:1 cold/hot line flow |
| 3.00 | Begin Linear Gradient | From 99:1 to 1:99 cold/hot line flow ratio |
| 6.00 | End Gradient | maintain 1:99 cold/hot line flow ratio |
| 16.00 | Begin Linear Gradient | return back to 99:1 cold/hot ratio in 1 min |

TABLE 4-continued

Mobile-Phase Conditions

| Time (min) | Parameter | Value |
|---|---|---|
| 17.00 | Initial Solvent Composition | Reestablished 99:1 cold/hot line flow ratio |

The chromatogram of the separated blend is shown in FIG. 8.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

We claim:

1. A liquid chromatography system for characterizing a sample, the system comprising a chromatographic column comprising an inlet port for receiving a mobile phase and the sample, and an effluent port for discharging the mobile phase and separated components of the sample from the chromatographic column, a detector in fluid communication with the effluent port of the chromatographic column for detecting a property of at least one of the sample components, an injection port for injecting the sample into the mobile phase, a fluid distribution system for controlling a composition and a temperature of the mobile phase, the fluid distribution system comprising: (i) a primary mixing zone adapted to mix a first primary feed and a second primary feed to form the mobile phase, the primary mixing zone being in fluid communication with the inlet port of the chromatographic column, (ii) a first secondary mixing zone adapted to mix a first secondary feed and a second secondary feed to form the first primary feed, the first secondary mixing zone being in fluid communication with the primary mixing zone, and (iii) a second secondary mixing zone adapted to mix a third secondary feed and a fourth secondary feed to form the second primary feed, the second secondary mixing zone being in fluid communication with the primary mixing zone, and a control system for controlling the composition and the temperature of the mobile phase by using one or more control protocols selected from the group consisting of: (a) varying relative flow rates of the secondary feeds supplied to the first secondary mixing zone, (b) varying relative flow rates of the secondary feeds supplied to the second secondary mixing zone, (c) varying relative flow rates of the first primary feed and the second primary feed supplied to the primary mixing zone, and (d) combinations thereof.

2. The liquid chromatography system of claim 1, further comprising a first line providing fluid communication between the first secondary mixing zone and the primary mixing zone, a first temperature control element in thermal communication with the first line for maintaining the first line at a first temperature, a second line providing fluid communication between the second secondary mixing zone and the primary mixing zone, and a second temperature control element in thermal communication with the second line for maintaining the second line at a second temperature different from the first temperature.

3. The liquid chromatography system of claim 2, wherein the first temperature control element is a resistive-heating element in adjacent proximity to the first line.

4. The liquid chromatography system of claim 2, wherein the second temperature control element is a fluid type heat exchanger, and the second line is located coaxially within an outer tube containing cooling fluid.

5. The liquid chromatography system of claim 1, wherein the system is automated.

6. A liquid chromatography system for characterizing a sample, the system comprising a chromatographic column comprising an inlet port for receiving a mobile phase and the sample, and an effluent port for discharging the mobile phase and separated components of the sample from the chromatographic column, a detector in selective fluid communication with the effluent port of the chromatographic column for detecting a property of at least one of the sample components, a fraction collector in selective fluid communication with the effluent port of the column, an injection port for injecting the sample into the mobile phase, a fluid distribution system for controlling a composition and a temperature of the mobile phase, the fluid distribution system comprising: (i) a primary mixing zone adapted to mix a first primary feed and a second primary feed to form the mobile phase, the primary mixing zone being in fluid communication with the inlet port of the chromatographic column, (ii) a first secondary mixing zone adapted to mix a first secondary feed and a second secondary feed to form the first primary feed, the first secondary mixing zone being in fluid communication with the primary mixing zone, and (iii) a second secondary mixing zone adapted to mix a third secondary feed and a fourth secondary feed to form the second primary feed, the second secondary mixing zone being in fluid communication with the primary mixing zone, and a control system for controlling the composition and the temperature of the mobile phase by using one or more control protocols selected from the group consisting of: (a) varying relative flow rates of the secondary feeds supplied to the first secondary mixing zone, (b) varying relative flow rates of the secondary feeds and supplied to the second secondary mixing zone, (c) varying relative flow rates of the first primary feed and the second primary feed supplied to the primary mixing zone, and (d) combinations thereof.

7. The liquid chromatography system of claim 6, further comprising a first line providing fluid communication between the first secondary mixing zone and the primary mixing zone, a first temperature control element in thermal communication with the first line for maintaining the first line at a first temperature, a second line providing fluid communication between the second secondary mixing zone and the primary mixing zone, and a second temperature control element in thermal communication with the second line for maintaining the second line at a second temperature different from the first temperature.

8. The liquid chromatography system of claim 7, wherein the first temperature control element is a resistive-heating element in adjacent proximity to the first line.

9. The liquid chromatography system of claim 7, wherein the second temperature control element is a fluid type heat exchanger, and the second line is located coaxially within an outer tube containing cooling fluid.

10. The liquid chromatography system of claim 6, wherein the system is automated.

11. A liquid chromatography system for characterizing a sample, the system comprising a first chromatographic column comprising an inlet port for receiving a mobile phase and the sample, and an effluent port for discharging the mobile phase and separated components of the sample from the first chromatographic column, a second chromatographic column comprising an inlet port for receiving the mobile phase comprising the sample, and an effluent port for discharging the mobile phase and separated components of the sample from the second chromatographic column, a detector in selective fluid communication with the effluent port of the first and second chromatographic columns for detecting a property of at least one of the sample components, a first injection port for injecting the sample into the mobile, phase, the first injection port in selective fluid communication with the inlet port of the first chromatographic column, a second injection port for injecting the sample into the mobile phase, the second injection port in selective fluid communication with the inlet port of the second chromatographic column, a fluid distribution system for controlling a composition and a temperature of the mobile phase, the fluid distribution system comprising: (i) a first primary mixing zone adapted to mix a first primary feed and a second primary feed to form the mobile phase, the primary mixing zone being in fluid communication with the inlet port of the first chromatographic column, (ii) a second primary mixing zone adapted to mix the first pry feed and the second primary feed to form the mobile phase, the second primary mixing zone being in fluid communication with the inlet port of the second chromatographic column, (iii) a first secondary mixing zone adapted to mix a first secondary feed and a second secondary feed to form the first primary feed, the first secondary mixing zone being in selective fluid communication with the first and second primary mixing zones, (iii) a second secondary mixing zone adapted to mix a third secondary feed and a fourth secondary feed to form the second primary feed, the second secondary mixing zone being in selective fluid communication with the first and second primary mixing zones, and (iv) a valve located between and in fluid communication with the first and second secondary mixing zones and the first and second primary mixing zones, and being adapted to direct the flow of the first and second primary feeds from the first and second secondary mixing zones to the first primary mixing zone, the second primary mixing zone, or both, and a control system for controlling the composition and the temperature of the mobile phase by using one or more control protocols selected from the group consisting of: (a) varying relative flow rates of the secondary feeds supplied to the first secondary mixing zone, (b) varying relative flow rates of the secondary feeds supplied to the second secondary mixing zone, (c) varying relative flow rates of the first primary feed and the second primary feed supplied to the first primary mixing zone, (d) varying relative flow rates of the first primary feed and the second primary feed supplied to the second primary mixing zone, and (e) combinations thereof.

12. The liquid chromatography system of claim 11, further comprising a first line providing fluid communication between the valve and the first primary mixing zone, a first temperature control element in thermal communication with the first line for maintaining the first line at a first temperature, a second line providing fluid communication between the valve and the first primary mixing zone, and a second temperature control element in thermal communication with the second line for maintaining the second line at a second temperature different from the first temperature.

13. The liquid chromatography system of claim 12, wherein the first temperature control element is a resistive-heating element in adjacent proximity to the first line.

14. The liquid chromatography system of claim 12, wherein the second temperature control element is a fluid type heat exchanger, and the second line is located coaxially within an outer tube containing cooling fluid.

15. The liquid chromatography system of claim 12, further comprising a third line providing fluid communication between the valve and the second primary mixing zone, a third temperature control element in thermal communication with the third line for maintaining the third line at a third temperature, a fourth line providing fluid communication between the valve and the second primary mixing zone, and a fourth temperature control element in thermal communication with the fourth line for maintaining the fourth line at a fourth temperature different from the third temperature.

16. The liquid chromatography system of claim 15, wherein the third temperature control element is a resistive-heating element in adjacent proximity to the third line.

17. The liquid chromatography system of claim 15, wherein the fourth temperature control element is a fluid type heat exchanger, and the fourth line is located coaxially within an outer tube containing cooling fluid.

18. The liquid chromatography system of claim 15, wherein the first and third temperature are the same temperature.

19. The liquid chromatography system of claim 15, wherein the first temperature is different from the third temperature.

20. The liquid chromatography system of claim 15, wherein the second and fourth temperature are the same temperate.

21. The liquid chromatography system of claim 15, wherein the second temperature is different from the fourth temperature.

22. The liquid chromatography system of claim 12, further comprising a fraction collector in selective fluid communication with the effluent ports of the first and second chromatographic columns.

23. The liquid chromatography system of claim 12, wherein a length of the second chromatographic column is at least one and a half times a length of the first chromatographic column.

24. The liquid chromatography system of claim 12, wherein an inner diameter of the second chromatographic column is at least one and a half times an inner diameter of the first chromatographic column.

25. The liquid chromatography system of claim 12, wherein an internal volume of the second chromatographic column is at least twice an internal volume of the first chromatographic column.

26. The liquid chromatography system of claim 12, wherein the system is automated.

27. A liquid chromatography system for characterizing a sample, the system comprising a chromatographic column comprising an inlet port for receiving a mobile phase and the sample, and an effluent port for discharging the mobile phase and separated components of the sample from the column, a detector in communication with the effluent port of the chromatographic column for detecting a property of at least one of the sample components, an injection valve proximately coupled to the inlet port of the chromatographic column, for injecting the sample with the mobile phase into the chromatographic column, the injection valve comprising: a primary mixing zone adapted to mix a first primary feed and a second primary feed to form the mobile phase, an injection port adapted for injecting the sample into the injection valve, and an outlet adapted for providing a flow path from the injection valve to the chromatographic column, wherein the outlet of the injection valve and the inlet port of the chromatographic column are proximately coupled, and a control system for controlling the temperature and the composition of the mobile phase by varying relative flow rates of the first primary feed and the second primary feed supplied to the primary mixing zone.

28. A liquid chromatography system for characterizing a sample, the system comprising a chromatographic column comprising an inlet port for receiving a mobile phase comprising the sample, and an effluent port for discharging the mobile phase and separated components of the sample from the column, a detector in selective communication with the effluent port of the chromatographic column for detecting a property of at least one of the sample components, a fraction collector in selective fluid communication with the effluent port of the column, an injection valve proximately coupled to the inlet port of the chromatographic column, for injecting the sample with the mobile phase into the chromatographic column, the injection valve comprising: a primary mixing zone adapted to mix a first primary feed and a second primary feed to form the mobile phase, an injection port adapted for injecting the sample into the injection valve, and an outlet adapted for providing a flow path from the injection valve to the chromatographic column, wherein the outlet of the injection valve and the inlet port of the chromatographic column are proximately coupled, and a control system for controlling the temperature and the composition of the mobile phase by varying relative flow rates of the fist primary feed and the second primary feed supplied to the primary mixing zone.

29. A liquid chromatography system for characterizing a sample, the system comprising: a chromatographic column comprising an inlet port for receiving a mobile phase and the sample, and an effluent port for discharging the mobile phase and separated components of the sample from the column, a fraction collector in fluid communication with the effluent port of the chromatographic column for collecting the separated components of the sample in separate vessels, an injection port in selective fluid communication with the inlet port of the chromatographic column for injecting the sample into the mobile phase, a mixing zone adaptable for mixing a first primary feed and a second primary feed to form the mobile phase, and in fluid communication with the inlet port of the chromatographic column, a first line for delivering the first primary feed to the mixing zone, a first temperature control element in thermal communication with the first line for maintaining the first line at a first temperature, a second line for delivering the second primary feed to the mixing zone, a second temperature control element in thermal communication with the second line for maintaining the second line at a second temperature different from the first temperature, and a control system for controlling the composition and the temperature of the mobile phase by using one or more control protocols selected from the group consisting of: (a) varying relative flow rates of one or more of the feeds, (b) varying the temperatures of the first and second lines, and (c) combinations thereof.

30. A liquid chromatography system for characterizing a sample, the system comprising a chromatographic column located in an ambient temperature environment, the column comprising an inlet port for receiving a mobile phase and the sample, and an effluent port for discharging the mobile phase and separated components of the sample from the chromatographic column, the chromatographic column adapted to be heated or cooled internally by the mobile phase in the absence of any heating chamber, a detector in fluid communication with the effluent port of the chromatographic column for detecting a property of at least one of the sample components, an injection port in selective fluid communication with the inlet port of the chromatographic column for injecting the sample into the mobile phase, a mixing zone adapted to mix a first primary feed and a second primary feed to form the mobile phase, and a control system for controlling a composition and a temperature of the mobile phase by varying the relative flow rates of one or more of the feeds.

31. The liquid chromatography system of claim 30, fiber comprising a first line in fluid communication with the mixing zone, adapted to deliver the first primary feed to the mixing zone, and a first temperature control element in thermal communication with the first line for maintaining the first line at a temperature above 100 degree C.

32. The liquid chromatography system of claim 31, further comprising a second line in fluid communication with the mixing zone, adapted to deliver the second primary feed to the mixing zone, and a second temperature control element in thermal communication with the second line for maintaining the second line at a temperature below 10 degrees C.

* * * * *